United States Patent
Berger et al.

(10) Patent No.: US 11,179,405 B2
(45) Date of Patent: Nov. 23, 2021

(54) NUTRITIONAL COMPOSITIONS FOR INFANTS AND/OR YOUNG CHILDREN COMPRISING OLIGOSACCHARIDES

(71) Applicant: NESTEC S.A., Vevey (CH)

(72) Inventors: Bernard Berger, Maracon (CH); Norbert Sprenger, Savigny (CH); Dominik Grathwohl, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/328,782

(22) PCT Filed: Aug. 24, 2017

(86) PCT No.: PCT/EP2017/071387
§ 371 (c)(1),
(2) Date: Feb. 27, 2019

(87) PCT Pub. No.: WO2018/046311
PCT Pub. Date: Mar. 15, 2018

(65) Prior Publication Data
US 2019/0209593 A1    Jul. 11, 2019

(30) Foreign Application Priority Data

Sep. 7, 2016    (EP) .................................. 16187699

(51) Int. Cl.
| | | |
|---|---|---|
| A61K 31/702 | (2006.01) | |
| A23L 33/00 | (2016.01) | |
| A23L 33/21 | (2016.01) | |
| A61K 45/06 | (2006.01) | |
| A61P 31/04 | (2006.01) | |
| A61P 1/00 | (2006.01) | |
| A61K 9/00 | (2006.01) | |

(52) U.S. Cl.
CPC ............ *A61K 31/702* (2013.01); *A23L 33/21* (2016.08); *A23L 33/40* (2016.08); *A61K 9/0056* (2013.01); *A61K 9/0095* (2013.01); *A61K 45/06* (2013.01); *A61P 1/00* (2018.01); *A61P 31/04* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2012/0171165 | A1* | 7/2012 | Buck | A61P 29/00 424/93.4 |
| 2012/0177691 | A1* | 7/2012 | Stahl | A23L 29/30 424/278.1 |
| 2013/0236424 | A1* | 9/2013 | Sprenger | A23L 33/40 424/93.4 |
| 2013/0251844 | A1 | 9/2013 | Sprenger et al. | |
| 2015/0031645 | A1* | 1/2015 | Buck | A61P 11/00 514/61 |
| 2016/0113952 | A1 | 4/2016 | Dekany | |
| 2017/0312298 | A1* | 11/2017 | Champion | C12P 19/18 |
| 2018/0042949 | A1* | 2/2018 | Sprenger | A61K 9/0056 |

FOREIGN PATENT DOCUMENTS

| | | |
|---|---|---|
| EP | 2465509 | 6/2012 |
| WO | 2015071402 | 5/2015 |
| WO | 2016066763 | 5/2016 |
| WO | 2016139328 | 9/2016 |
| WO | 2017021476 | 2/2017 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Salvini et al. "Probiotics, Prebiotics and Child Health: Where Are We Going?" The Journal of International Medical Research, 2004, vol. 32, pp. 97-108.
Looijer-Van Langen et al. "Prebiotic Feeding in Rodents Stimulated Growth of Intestinal Pediococci with Bactericidal Effects Against Clostridium difficile" Gastroenterology, vol. 136, No. 5, May 1, 2009, pp. A-772.
Karpova, "Necrotizing enterocolitis in new-borns: clinical picture, diagnosing and treatment", STM Journal, 2012, vol. 2, pp. 138 to 142.
Office Action Received for RU Application No. 2019109938, dated Apr. 29, 2020, 14 pages.

* cited by examiner

*Primary Examiner* — Dale R Miller
(74) *Attorney, Agent, or Firm* — K&L Gates LLP

(57) ABSTRACT

The present invention relates to nutritional compositions for infants or young children and their health effects, that comprise at least one fucosylated oligosaccharide and at least one N-acetylated oligosaccharide. These nutritional compositions are for use to prevent and/or treat infection in an infant or young child, by promoting and/or reducing specific microbiota communities in an infant or young child.

19 Claims, 12 Drawing Sheets

NUTRITIONAL COMPOSITIONS FOR INFANTS AND/OR YOUNG CHILDREN COMPRISING OLIGOSACCHARIDES

CROSS REFERENCE TO RELATED APPLICATIONS

The present application is a National Stage of International Application No. PCT/EP2017/071387, filed on Aug. 24, 2017, which claims priority to European Application No. 16187699.0, filed on Sep. 7, 2016, the entire contents of which are being incorporated herein by reference.

FIELD OF THE INVENTION

The present invention relates to nutritional compositions for infants or young children and their health effects. In particular, it relates to nutritional compositions comprising specific oligosaccharides for use to prevent and/or treat infection in an infant or young child, by promote and/or reduce specific microbiota communities in an infant or young child.

BACKGROUND OF THE INVENTION

Mother's milk is recommended for all infants. However, in some cases breast feeding is inadequate or unsuccessful for medical reasons or the mother chooses not to breast feed. Nutritional compositions such as infant formulae have been developed for these situations.

Nutritional compositions for infants and young children are often sold as powders to be reconstituted with water or in some instances as ready to drink or concentrated liquid compositions. Those compositions are intended to cover most or all the nutritional needs of the infants or young children.

It is known however, that human breast milk represents the ultimate gold standard in terms of infants' nutrition. Infant formula manufacturers have therefore made many attempts to induce nutritional health effects close to or similar to the benefits of human breast milk. However many studies have shown that infant formula do not induce the identical effects on the body compared to human breast milk. For example, infants fed infant formula and infants fed human-breast milk (HBM) can exhibit a different intestinal (gut) microbiota.

Infancy, especially the first weeks, 3 months, 6 months or 12 months of life is a critical period for the establishment of a balanced gut microbiota.

It is know that the modulation of the gut microbiota during infancy can prospectively have a great influence in the future health status of the bodies. For example the gut flora can have influence on the development of a strong immune system later in life, a normal growth and even on the development of obesity later in life.

Similarly, a healthy intestinal flora is an indicator of the health of an infant and an altered intestinal microbiota can be an indicator (and/or a cause) of abnormal health events such as diarrhoea, under-absorption of nutrients, colic, altered sleep and/or altered growth and development.

It is known that the mode of delivery can also affect the initial gut microbiota of infants: infants delivered by Caesarean section (C-section) have been shown to have a different gut microbiota compared to vaginally-delivered infants.

The gut microbiota and its evolution during the development of the infant is, however, a fine balance between the presence and prevalence (amount) of many populations of gut bacteria. Some gut bacteria are classified as "generally positive" while other ones are "generally negative" (or pathogenic) as to their effect on the overall health of the infant.

Certain species of "generally positive" bacteria, such as bifidobacteria, may be under-represented in infants fed conventional infant formula in comparison to breast fed infants. Similarly some bacterial populations are considered pathogenic and should remain of low prevalence in the gut microbiota.

Indeed infant fed infant formulae may not benefit from the natural, well balanced intestinal gut flora (gut microbiota) of infants fed exclusively or predominantly Human Breast Milk. Such natural microbiota observed in breast fed infants is indeed both very well controlled over time (evolution over time) and complex. Many taxa of micro-organisms co-exist in the highly complex microenvironment of the gut/intestine, each in sequentially defined proportions. Quantitative and qualitative dimensions are to be considered when defining the microbiota of infants or young children. Furthermore, the variation over time of the gut microbiota adds to the complexity.

A suitable and healthy gut microbiota is a key factor in the development of the mucosal immune system of the infant. While many studies have identified ways to promote the growth and prevalence of some positive bacteria in the gut of infants, little is known about ways to induce the specific microbiota profile which protects from infection.

There is a need for nutritional compositions for infants or young children that promote and/or induce specific microbiota communities that will protect against infection.

There is a need to provide infants or young children with the best nutrition that enables the development of specific microbiota communities which protect against infection, said development being short term (i.e. during the nutritional intervention) and/or long term (i.e. after the nutritional intervention).

There is a need for nutritional compositions for infants or young children that induce an optimal short term or long term health status through a nutrition inducing and/or promoting development of specific microbiota communities which protect against infection; such health status including an optimum growth over time, and an optimum development of the immune system, as well as the prevention of metabolic disorders.

There is a need to compensate for the sub-normal specific microbiota communities observed in non-breast-fed infants or young children, e.g. those fed a conventional nutritional composition. There is a need to rebalance such overall microbiota.

There is a need to deliver such health benefits in these infants or young children in a manner that does not induce side effects and/or in a manner that is easy to deliver, and well accepted by the parents or health care practitioners.

SUMMARY OF THE INVENTION

The present invention relates in one aspect to a nutritional composition comprising at least one fucosylated oligosaccharide and at least one N-acetylated oligosaccharide, for use to prevent and/or treat infection by promoting in an infant or young child a Community type B and/or by reducing a Community type C, wherein Community type B is defined as a microbiota community comprising at least 80% Bifidobactera (% relative abundance);

Community type C is defined as a microbiota community comprising from 50 to 80% Bifidobacteria (% relative abundance), and further comprising one or more of Firmicutes, Bacteroidetes and/or Proteobacteria; and
wherein said promoting or reducing is in comparison to the microbiota in the gut of infants or young children fed predominantly or exclusively with the conventional nutritional composition not comprising said oligosaccharides.

Another aspect of the present invention relates to a method of preventing and/or treating infection in an infant or young child by providing a nutritional composition according to the invention.

Figure 1:
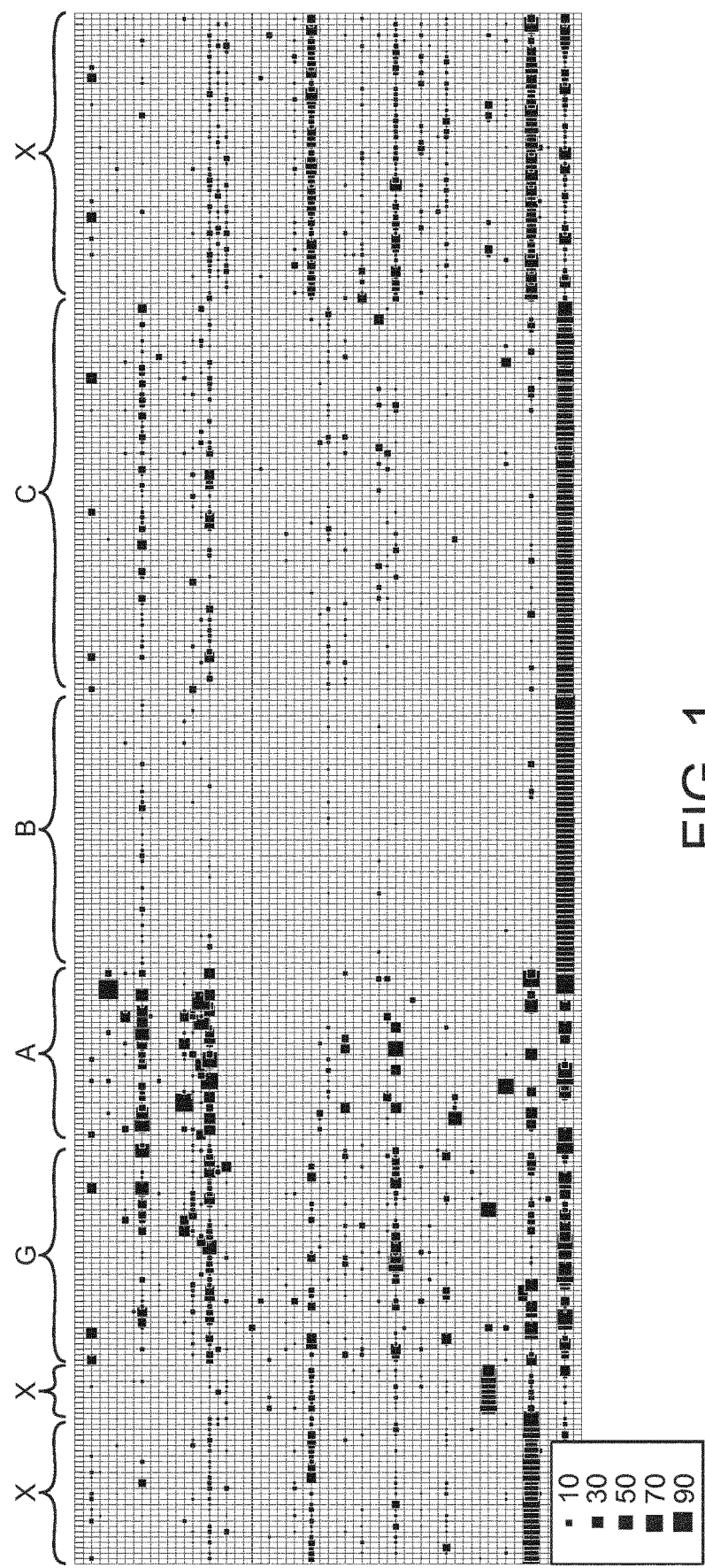
FIG. 1 shows an overview of the grouping of microbiota in samples to community types. Samples are depicted by horizontal lines and taxa on vertical lines, with squares representing their relative amount in each sample (scale at bottom right) The numbers refer to community types.

The present invention will now be described in more detail in the following.

DETAILED DESCRIPTION OF THE INVENTION

Definitions

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "Infant or young child vaginally born" means an infant or young child who was vaginally delivered and not delivered by caesarean.

A "preterm" or "premature" means an infant or young child who was not born at term. Generally, it refers to an infant or young child born prior to the completion of 37 weeks of gestation.

By the expression "small for gestational age" or "SGA", it is intended to mean an infant or young child who is smaller in size than normal for their gestational age at birth, most commonly defined as a weight below the 10th percentile for the gestational age. In some embodiments, SGA may be associated with Intrauterine growth restriction (IUGR), which refers to a condition in which a foetus is unable to achieve its potential size.

By the expression "low birth weight", it should be understood as any body weight under 2500 g at birth.

The expression "nutritional composition" means a composition which nourishes a subject. This nutritional composition is usually to be taken orally or intravenously, and it usually includes a lipid or fat source, a carbohydrate source and a protein source.

In a particular embodiment the nutritional composition of the present invention is an hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter Infant formula" and "follow-up formula" or "follow-on formula". In some embodiments, the infant formula is a preterm formula.

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life, and comprising a cereal component.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "X days/weeks/months/years of age", "X days/weeks/months/years of life" and "X days/weeks/months/years of birth" can be used interchangeably.

The "mother's milk" should be understood as the breast milk or colostrum of the mother. HBM refers to Human Breast Milk.

The expressions "infants/young children fed exclusively with human breast milk", "infants or young children exclusively breast fed", "exclusive breast fed infants or young children" and "breast-fed infants/young children" can be used interchangeably. They refer to infants or young children fed with a great majority (i.e. at least 90%, or at least 95%, or at least 99%) or all (100%) of nutrients and/or energy originating from human breast milk.

The expression "infants or young children exclusively fed nutritional compositions" refers to infants or young children fed with a great majority (i.e. at least 90%, or at least 95%, or at least 99%) or all (100%) of nutrients and/or energy originating from synthetic nutritional compositions such as infant formula, follow-up milks or growing-up milks.

The expression "infants or young children predominantly fed nutritional compositions" refers to infants or young children fed with nutritional sources of nutrients and/or energy predominantly originating from synthetic nutritional compositions such as infant formula, follow-up milks or growing-up milks. Predominantly refers to at least 50% (or at least 60% or at least 75%) of those nutrients and/or energy, such as from 50% to 90%, or from 60% to 80%.

The expression "conventional nutritional composition" refers to standard synthetic nutritional compositions such as infant formula, follow-up milks or growing-up milks already found in the market. A "conventional nutritional composition not comprising said oligosaccharides" refers to a standard nutritional composition that does not comprise the "at least one fucosylated oligosaccharide and at least one N-acetylated oligosaccharide".

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or an infant cereal product or any other formulation designed for infant nutrition). They can also be expressed in g/100 kcal.

An "oligosaccharide" is a saccharide polymer containing a small number (typically three to two) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2' fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) and any combinations thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The expression "promoting and/or inducing" in infants or young children a refers to the development, the increase, the establishment, the apparition and/or the shifting of a particular microbiota community in said infants or young children.

The terms "microbial", "microflora" and "microbiota" can be used interchangeably.

The expressions "microbiota in the gut", "microbiota of the gut", "gut microbiota" and "intestinal microbiota" can be used interchangeably.

The expression "Community type" refers to a set of bacteria present in taxa proportions as defined by the Dirichlet Multinomial Mixtures modeling framework (see further Examples for references) which best describes a duster of samples showing similar microbiota compositions (ie, proportions or relative abundance of different bacterial taxa in the population).

Community type B is defined as a microbiota community comprising almost exclusively Bifidobacteria, such as at least 80% Bifidobacteria (% relative abundance); for example from 80 to 95%, such as 85 to 93%, such as about 90% Bifidobacteria.

Community type C is defined as a microbiota community which is dominated by Bifidobacteria and also showing a substantial proportion of other taxonomic groups belonging to Firmicutes, Bacteroidetes and/or Proteobacteria; for example Community type C may be defined as comprising from 40 to 80% Bifidobacteria (% relative abundance, such as from 50 to 80%, such as from 60 to 80%, for example 65 to 75%, or about 70%, relative abundance) as well as one or more selected from the group consisting of Firmicutes, Bacteroidetes and Proteobacteria.

A community type may in other words be described as a subpopulation of the microbiota, the subpopulation defined by applying the Dirichlet Multinomial Mixtures modeling framework.

Relative abundance means the amount in relation to the total amount. Thus, 80% relative abundance means 80% of the microbiota, irrespective of how the total microbiota is measured. Total microbiota may be measured for example by mass, counts, etc.

A microbiota community means a subpopulation of a microbiota.

In some embodiments of the invention, the Community Type B and Community Type C respectively, comprises or consists of the bacteria as shown in the examples and figures.

The expressions "down regulation" and "reduction" can be used interchangeably.

By the expressions "preventing" or "prevention", it is meant avoiding that a physical state, a condition or their consequences occurs and/or decreasing its incidence (i.e. reduction of the frequency).

By the expressions "treating" or "treatment", it is meant a decrease of the duration and/or of the severity of a physical state, a condition or their consequences.

The prevention and/or the treatment of a physical state, a condition or their consequences can occur during the treatment (i.e. during the administration of the composition of the present invention, either immediately after the start of the administration or some time after, e.g. some days or weeks after the start). But it can also encompass the prevention and/or the treatment later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. Dietary modulation of the human colonic microbiota: introducing the concept of prebiotics. J Nutr. 1995; 125:1401-12).

The term "probiotic" means microbial cell preparations or components of microbial cells with a beneficial effect on the health or well-being of the host. (Salminen S, Ouwehand A. Benno Y. et al. "Probiotics: how should they be defined" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising at least one fucosylated oligosaccharide and at least one N-acetylated oligosaccharide for use to prevent and/or treat infection by promoting in an infant or young child a Community type B and/or to by reducing a Community type C, in an infant or young child, wherein Community type B is defined as a microbiota community comprising at least 80% Bifidobactera (% relative abundance);

Community type C is defined as a microbiota community comprising from 40 to 80% Bifidobacteria, and further comprising one or more of Firmicutes, Bacteroidetes and/or Proteobacteria;

wherein said promoting or reducing is in comparison to the microbiota in the gut of infants or young children fed predominantly or exclusively with the conventional nutritional composition not comprising said oligosaccharides.

Alternatively, the invention may be described as relating to a nutritional composition comprising at least one fucosylated oligosaccharide and at least one N-acetylated oligosaccharide, for use to prevent and/or treat infection in an infant or young child, by promoting a Community B and/or reducing a Community C, wherein said promotion involves an up-regulation of the population of *Bifidobacterium* and said reduction involves a down regulation of the populations of *Escherichia* and/or Peptostreptococcaceae, in comparison to the microbiota in the gut of infants or young children fed predominantly or exclusively with the conventional nutritional composition not comprising said oligosaccharides, and prevent and/or treat infection.

Fucosylated Oligosaccharide

The nutritional composition of the present invention comprises at least one fucosylated oligosaccharide. There can be one or several types of fucosylated oligosaccharide(s). The fucosylated oligosaccharide(s) may be selected from the group consisting of 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difucolacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list consisting of 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used.

Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

N-Acteylated Oligosaccharide

The nutritional composition of the present invention also comprises at least one the N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6.

In a preferred embodiment, the nutritional composition according to the invention comprises lacto-N-neotetraose (LNnT). In a particular embodiment, there is no other type of N-acetylated oligosaccharide than lacto-N-neotetraose (LNnT), i.e. the nutritional composition of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the nutritional composition comprises 2'-fucosyllactose (2FL) and lacto-N-neotetraose (LNnT).

In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

Amounts of Fucosylated Oligosaccharide and N-Acetylated Oligosaccharide

In the present invention, the fucosylated oligosaccharide(s) and N-acetylated oligosaccharide(s) are present in the nutritional composition in some particular amounts. The term "amount" refers to the total amount of each of these 2 components in the nutritional composition unless otherwise specified. It therefore does not refer to an individual amount except when there is a single type of these components (in that case both the total and individual amounts equal). By way of illustrative example, if there is only one (i.e. only one type of) fucosylated oligosaccharide in the composition (e.g. 2FL), its individual amount (and therefore the total amount of fucosylated oligosaccharides) will be in the range 0.5-2.0 g/L. If there are several (i.e. several types of) fucosylated oligosaccharides, their individual amount will be lower (e.g. if there are 2 different types of fucosylated oligosaccharide, e.g. 2FL+3FL, there may be for example each in an individual amount of 0.5 g/L) but the total amount of fucosylated oligosaccharides will be in the range 0.5-2.0 g/L.

The fucosylated oligosaccharide(s) can be present in the nutritional composition according to the present invention in a total amount of 0.75-1.65 g/L of the composition. In some embodiments, the fucosylated oligosaccharide(s) may be in a total amount of 0.8-1.5 g/L of the composition, such as 0.85-1.3 g/L or 0.9-1.25 g/L or 0.9-1.1 g/L or 1-1.25 g/L or 1.05-1.25 g/L of the composition. In some embodiments, the fucosylated oligosaccharide(s) may be in a total amount of 0.15-2 g/L of the composition, such as 0.2-1.5 g/L. In a particular embodiment, the fucosylated oligosaccharide(s) is/are in a total amount of 1 g/L of the composition. In another particular embodiment, the fucosylated oligosaccharide(s) is/are in a total amount of 1.24 g/L of the composition.

The fucosylated oligosaccharide(s) can be present in the nutritional composition in a total amount of 0.52-1.15 g/100 g of composition on a dry weight basis. The fucosylated oligosaccharide(s) may be in a total amount of 0.55-1.05 g/100 g of the composition, such as 0.59-0.9 g/100 g, or 0.62-0.87 g/100 g or 0.62-0.77 g/100 g or 0.69-0.87 g/100 g or 0.73-0.87 g/100 g of the composition. The fucosylated oligosaccharide(s) may be in a total amount of 0.1-1.8 g/100 g of the composition, such as 0.15-0.9 g/100 g. In a particular embodiment, the fucosylated oligosaccharide(s) is/are in a total amount of 0.69 g/100 g of the composition. In another particular embodiment, the fucosylated oligosaccharide(s) is/are in a total amount of 0.86 g/100 g of the composition.

The N-acetylated oligosaccharide(s) can be present in the nutritional composition according to the present invention in a total amount of 0.45-0.85 g/L of the composition.

In some embodiments, the N-acetylated oligosaccharide(s) may be in a total amount of 0.5-0.8 g/L of the composition, such as 0.5-0.75 g/L or 0.5-0.7 g/L of the composition. In some embodiments, the N-acetylated oligosaccharide(s) may be in a total amount of 0.05-0.8 g/L of the composition, such as 0.1-0.5 g/L or 0.1-0.3 g/L of the composition. In a particular embodiment, the N-acetylated oligosaccharide(s) is/are in a total amount of 0.5 g/L or 0.1 g/L of the composition (or at least those amounts). In another particular embodiment, the N-acetylated oligosaccharide(s) is/are in a total amount of 0.63 g/L of the composition.

The N-acetylated oligosaccharide(s) can be present in the nutritional composition in a total amount of 0.31-0.59 g/100 g of composition on a dry weight basis. The N-acetylated oligosaccharide(s) may be in a total amount of 0.35-0.56 g/100 g of Composition, such as 0.35-0.52 g/100 g or 0.35-0.49 g/100 g. The n-acetylated Oligosaccharide(s) may be in a total amount of 0.04-0.65 g/100 g of composition, Such as 0.05-0.5 g/100 g or 0.05-0.1 g/100 g. In a particular embodiment, the n-acetylated oligosaccharide(s) is/are in a total amount of 0.35 g/100 g or 0.07 g/100 g of the composition (or at least those amounts). In another particular embodiment, the N-acetylated oligosaccharide(s) is/are in a total amount of 0.44 g/100 g of the composition.

Therefore in one embodiment of the present invention, the nutritional composition comprises at least one fucosylated oligosaccharide and at least one N-acetylated oligosaccharide wherein:

the fucosylated oligosaccharide(s) is/are in a total amount of 0.8-1.5 g/L of the composition and/or in a total amount of 0.55-1.05 g/100 g of composition on a dry weight basis; and/or the N-acetylated oligosaccharide(s) is/are in a total amount of 0.5-0.8 g/L of the composition and/or in a total amount of 0.35-0.56 g/100 g of composition on a dry weight basis.

In another particular embodiment the nutritional composition of the present invention comprises at least one fucosylated oligosaccharide and at least one N-acetylated oligosaccharide wherein:

the fucosylated oligosaccharide(s) is/are in a total amount of 0.85-1.3 g/L of the composition and/or in a total amount of 0.59-0.9 g/100 g of composition on a dry weight basis; and/or the N-acetylated oligosaccharide(s) is/are in a total amount of 0.5-0.75 g/L or 0.08-0.6 g/L of the composition and/or in a total amount of 0.35-0.52 g/100 g or 0.1-0.5 g/100 g of composition on a dry weight basis.

In another particular embodiment the nutritional composition of the present invention comprises at least one fucosylated oligosaccharide and at least one N-acetylated oligosaccharide wherein:

the fucosylated oligosaccharide(s) is/are in a total amount of 1-1.25 g/L of the composition and/or in a total amount of 0.69-0.87 g/100 g of composition on a dry weight basis; and/or the N-acetylated oligosaccharide(s) is/are in a total amount of 0.5-0.7 g/L of the composition and/or in a total amount of 0.35-0.49 g/100 g of composition on a dry weight basis.

In another particular embodiment the nutritional composition of the present invention comprises at least one fucosylated oligosaccharide and at least one N-acetylated oligosaccharide wherein:

the fucosylated oligosaccharide(s) is/are in a total amount of 1.05-1.25 g/L of the composition and/or in a total amount of 0.73-0.87 g/100 g of composition on a dry weight basis; and/or the N-acetylated oligosaccharide(s) is/are in a total amount of 0.5-0.7 g/L of the composition and/or in a total amount of 0.35-0.49 g/100 g of composition on a dry weight basis.

In a specific embodiment the nutritional composition according to the invention comprises at least one fucosylated oligosaccharide and at least one N-acetylated oligosaccharide wherein:

the fucosylated oligosaccharide(s) is/are in a total amount of 1 g/L of the composition and/or in a total amount of 0.69 g/100 g of composition on a dry weight basis; and/or the N-acetylated oligosaccharide(s) is/are in a total amount of 0.5 g/L of the composition and/or in a total amount of 0.35 g/100 g of composition on a dry weight basis.

In another specific embodiment the nutritional composition according to the invention comprises at least one fucosylated oligosaccharide and at least one N-acetylated oligosaccharide wherein:

the fucosylated oligosaccharide(s) is/are in a total amount of 1.24 g/L of the composition and/or in a total amount of 0.86 g/100 g of composition on a dry weight basis; and/or the N-acetylated oligosaccharide(s) is/are in a total amount of 0.63 g/L of the composition and/or in a total amount of 0.44 g/100 g of composition on a dry weight basis.

The fucosylated oligosaccharide(s) and the N-acetylated oligosaccharide(s) comprised in the nutritional composition according to the invention are typically present in a ratio fucosylated oligosaccharide(s):the N-acetylated oligosaccharide(s) of from 2:0.54 to 2:2.26, such as 2:0.76-2:1.8 or 2:0.8-2:1.4. In a particularly advantageous embodiment, this ratio is 2:1 or around 2:1. In another particularly advantageous embodiment this ratio is 10:1 or between 15:1 and 2:1.

Other Oligosaccharides

The nutritional composition according to the present invention may also comprise at least another oligosaccharide(s) (i.e. other than the fucosylated oligosaccharide(s) and N-acetylated oligosaccharide(s) necessarily present in the composition) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition. In a particular embodiment, the nutritional composition can also contain at least one bovine milk oligosaccharide (BMO).

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®. The FOS can be long chain FOs or short chain FOS; preferably FOs is short chain FOS.

Oligofructose

In a particular embodiment, the nutritional composition according to the invention can comprise at least about 0.4 g or at least 0.7 g of oligofructose per 100 kcal of the composition such as from about 0.4 to about 0.9 g, from about 0.4 to about 0.7 g, from about 0.4 to about 0.5 g, from about 0.7 to about 0.8 g, or from about 0.7 to about 0.9 g oligofructose per 100 kcal.

In some embodiments the oligofructose has a degree of polymerization of from 2 to 10. In some embodiments, at least 80%, 90%, 95%, 99% or 100% of the oligofructose has a degree of polymerization of from 2 to 8 (between 2 and 8).

In a particular embodiment, the nutritional composition according to the invention can comprise GOS. A galacto-oligosaccharide is an oligosaccharide comprising two or more galactose molecules which has no charge and no N-acetyl residue. Suitable galacto-oligosaccharides that may also be added in the nutritional composition according to the present invention include Galbeta1,3Galbeta1,4Glc, Gal1,6Galbeta1,4Glc, Galbeta1,3Galbeta1,3Galbeta1,4Glc, Galbeta1,6Galbeta1,6Gal beta 1,4Glc, Gal beta 1,3Gal beta 1,6Gal beta 1,4Glc, Gal beta 1,6Gal beta 1,3Gal beta 1,4Glc, Gal beta 1,6Gal beta 1,6Gal beta 1,6Glc, Gal beta 1,3Gal beta 1,3Glc, Gal beta 1,4Gal beta 1,4Glc and Gal beta 1,4Gal beta 1,4Glc but also any mixture thereof. Synthesized galacto-oligosaccharides such as Gal beta 1,6Gal beta 1,6Gal beta 1,4Glc, Gal beta 1,6Gal beta 1,6Glc, Gal beta 1,3Gal beta 1,4Glc, Gal beta 1,6Gal beta 1,6Gal beta 1,4Glc, Gal beta 1,6Gal beta 1,3Gal beta 1,4Glc, Gal beta 1,3Gal beta 1,6Gal beta 1,4Glc, Gal beta 1,4Gal beta 1,4Glc and Gal beta 1,4Gal beta 1,4Gal beta 1,4Glc and mixture thereof are commercially available under trademarks Vivinal and Elix' or. Other suppliers of oligosaccharides are Dextra Laboratories, Sigma-Aldrich Chemie GmbH and Kyowa Hakko Kogyo Co., Ltd. Alternatively, specific glycotransferases, such as galoctosyltransferases may be used to produce neutral oligosaccharides.

In a particular embodiment, the nutritional composition can also contain at least one bovine milk oligosaccharide. Conventional technologies for fractioning and enriching bovine milk fractions in bovine milk derived oligosaccharides can be used (such conventional technologies include column filtration, resin-filtration, nano-filtration, enzymatic treatment specially with beta-galactosidase, precipitation of proteins, crystallisation and separation of lactose etc, . . . ). Some fractions of bovine milk enriched in oligosaccharides are commercially available or have been described for example in EP2526784 A1.

Sialylated Oligosaccharide(s)

In a particular embodiment, the nutritional composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10.

In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s). In some particular embodiments the composition can comprise from 0.8 to 1.7 g/l of sialylated oligosaccharide(s).

The composition according to the invention can contain from 0.03 to 3.88 g of sialylated oligosaccharide(s) per 100 g of composition on a dry weight basis, e.g. 0.08-3.10 g or 0.23-1.55 g or 0.31-1.16 g or 0.31-0.77 g or 0.39-0.7 g or 0.62-1.32 g of sialylated oligosaccharide(s) per 100 g of composition on a dry weight basis.

In some particular embodiments of the present invention, the nutritional composition comprises sialylated oligosaccharide(s) in an amount of below 0.1 g/100 g of composition on a dry weight basis.

In some particular embodiments of the present invention, the nutritional composition does not contain any sialylated oligosaccharide(s).

In a particular embodiment, the nutritional composition may also additionally comprise an oligosaccharide mixture ("BMOS") that comprises from 0.1 to 4.0 wt % of N-acetylated oligosaccharide(s), from 92.0 to 98.5 wt % of the galacto-oligosaccharide(s) and from 0.3 to 4.0 wt % of the sialylated oligosaccharide(s).

Precursors

The composition according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide.

The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

Probiotics

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BUS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

In a particular embodiment the probiotic is a *Bifidobacterium lactis*, such as *Bifidobacterium lactis* CNCM 1-3446.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, Haemophilus, Moraxella and Staphylococci.

The nutritional composition according to the invention can be for example an infant formula, a starter infant formula, a follow-on or follow-up formula, a preterm formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

Protein

The nutritional composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.1 g per 100 kcal, e.g. between 1.8 to 2.1 g/100 kcal, or 1.8-2 g/100 kcal or 1.9-2.1 g protein per 100 kcal, or in an amount below 1.8 g per 100 kcal such as 1.4-1.8 g/100 kcal or 1.5-1.7 g/100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

"Alpha-Lactalbumin" refers to a high-quality, easy-to-digest whey protein that comprises 20-25% of total human breast milk (HBM) protein and is the primary protein found in HBM. The structure of alpha-lactalbumin is comprised of 123 amino acids and 4 disulfide bridges and the protein has a molecular weight of 14.2K Daltons. Alpha-lactalbumin is ideal for lower protein infant formulas due to its high content of essential amino acids, particularly tryptophan. In one embodiment, the nutritional composition of this invention comprises alpha-lactalbumin in an amount of from about 0.2 to about 0.4 g/100 kcal of the nutritional composition, or in an amount of at least 1.7 g/L, or at least 2.0 g/L or at least 2.3 g/L, or at least 2.6 g/L of the nutritional composition.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully (i.e. extensively) or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

Lipids

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

In one embodiment, the nutritional composition of this invention comprises triglycerides with high sn-2 palmitate, preferably triglycerides having more than 33% of the palmitic acids in sn-2 position.

In one embodiment, the nutritional composition of this invention comprises about 5 or 6 g per 100 kcal of fat, and for example at least about 7.5 wt % of this fat, for example, about 7.5-12.0%, consists of palmitic acid in the sn-2 position.

In one embodiment, of the invention the composition comprises at least 7.5%, preferably 8%, more preferably at least 9.6% of the fat is sn-2 palmitate, for example about 7.8-11.8%, about 8.0-11.5 wt %, about 8.5-11.0% or about 9.0-10.0 wt % of the fat is palmitic acid in the sn-2 position of a triglyceride.

In some embodiments, palmitic acid comprises from about 15 to about 25%, such as from about 15 to about 20%, of the total fatty acids content of the formula, by weight, and at least from about 30%, for example, from about 35 to about 43% of the total palmitic acid content is in the sn-2 position.

A commercially available composition sold by Lipid Nutrition is Betapol™ B-55, which is a triglyceride mixture derived from vegetable oil in which at least 54% of the palmitic acid is in the sn-2 position of the glycerol molecule. In one embodiment, the nutritional composition of the invention comprises a fat content that is about 40-50% Betapol™ B-55 by weight, for example, from about 43% to about 45% by weight. Those skilled in the art will appreciate that the percentage of the high sn-2 fat used and the total amount of sn-2 palmitate in the formula may vary, and that a different high sn-2 palmitate oil may be used, without departing from the spirit and scope of the invention.

Vitamins and Minerals

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation.

Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

Infants or Young Children

The nutritional composition according to the invention is for use in infants or young children. It may be particularly adapted for infants under 6 months of age.

The infants or young children may be born term or preterm. In a particular embodiment the nutritional composition of the invention is for use in infants or young children that were born preterm. In a particular embodiment the nutritional composition of the invention is for use in preterm infants.

In one embodiment, the nutritional composition of the present invention may also be used in an infant or a young child that was born small for gestational age or low birth weight.

Infants or young children with low birth weight may or may not be preterm, and similarly, infants or young children who are small for gestational age may or may not be preterm.

The nutritional composition of the present invention may also be used in an infant or a young child that was born by C-section or that was vaginally delivered.

All infants and young children can benefit from the invention as all of them are or can be, at a certain age, susceptible to acquiring an infection.

In some advantageous embodiments of the invention, the nutritional composition in for use infants or young children having a fragile immune system, such as preterm infants, infants born by Caesarean-section, infants born small for gestational age or with low birth weight, hospitalized infants/young children, and/or infants/young children treated or having been treated by antibiotics, and/or infants/young children suffering or having suffered from gut infection and/or gut inflammation.

It is indeed foreseen that the composition of the invention may be even more beneficial to infants born with possibly impaired immune system or fragile infants/young children (such as prematurely born infants and/or infants born by C-section). It is also foreseen that the composition of the invention may be even more beneficial to infants/young children exhibiting intestinal disorders (such as diarrhoea, infections or colic), especially after birth, for example, during the first 4 weeks after birth.

In embodiments of the invention, the infants born prematurely or born by caesarean section or born small for gestational age or with low birth weight, or suffering or having suffered from gut infection and/or gut inflammation, are targeted by the composition of the present invention, and especially when the infants are 0-6 months of age. Without being bound by the theory, it is believed that younger infants benefit even more from the composition of the invention, especially when the infants have (or are at risk of having) a fragile health condition (as exemplified by the conditions cited above).

In some embodiments the composition according to the invention can be for use before and/or during the weaning period.

In one embodiment, the infants or young children are 0-36 months of age, such as 0-12 months or 0-6 months of age. It is foreseen that the composition of the invention may be even more beneficial to infants just after birth (0-4 weeks or 0-8 weeks) as their immune system may be more fragile.

The nutritional composition can be administered (or given or fed) at an age and for a period that depends on the needs.

The nutritional composition of the present invention may be used for prevention or treatment purposes:
in reducing fever in an infant or a young child by promoting Community type B and/or reducing Community C;
in reducing the use of antibiotics in an infant or a young child (during the period of administration of the composition and/or after the period of administration);
in reducing the use of antipyretics in an infant or a young child; and/or
in preventing and/or treating diseases/conditions involving fever and/or the administration of antibiotics or of antipyretics in an infant or a young child,
in promoting Community type B and/or reducing Community type C thereby preventing and/or treating infections.

In some particular embodiments, the nutritional composition can be an infant formula and may be especially intended for infants between 0 and 12 months of age fed predominantly with infant formula. In some embodiments the nutritional composition is used for prevention purposes. The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, . . . ), or few months (e.g. 1, 2, 3, 4, 5, 6, 7, 8, 9, 10 . . . ) after birth. This may be especially the case when the infant is premature, but not necessarily.

The nutritional composition of the present invention may be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs.

In one embodiment the composition of the invention is given to the infant or young child as a supplementary composition to the mother's milk. In some embodiments the infant or young child receives the mother's milk during at least the first 2 weeks, or the first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the 1st, 2nd or 4th month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

In some other embodiments the nutritional composition according to the present invention is given for treatment purposes. This will more be the case when the cn is used for the treatment of infections, or for the promotion of Community type B and/or the reduction of Community C.

In these cases, the nutritional composition may be given may be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs. It may be given once the symptoms appear or once these health diseases/conditions have been diagnosed. It may be given up to the symptoms of the treated diseases/conditions disappear, or several days/weeks/months after said disappearance.

The present inventors have also found that the particular nutritional composition according to the invention is particularly efficient in reducing fever and in reducing the use (i.e. administration) of antibiotics and of antipyretics in an infant or a young child.

The nutritional composition according to the invention may thus also be used in reducing fever and/or in promoting Community type B and/or reducing community C, thereby reducing the use of antibiotics and of antipyretics in the infant or young child.

In a particular aspect, the present invention also refers to a nutritional composition comprising at least one fucosylated oligosaccharide and at least one N-acetylated oligosaccharide, for use to promote or increase Community type B and/or reduce Community type C in the gut of an infant or young child, thereby reducing fever and/or reducing the administration of antibiotics and/or reducing the use of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population . . . ) also apply for this aspect.

In another particular aspect, the present invention also refers to a nutritional composition comprising at least one fucosylated oligosaccharide and at least one N-acetylated oligosaccharide, for use to promote or increase Community A and/or reduce Community type B in the gut of an infant or young child, thereby preventing and/or treating diseases/conditions (e.g. infections, inflammations . . . ) involving fever and/or the administration of antibiotics or of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population . . . ) also apply for this aspect.

Discussion of Health Benefits

The nutritional composition of the present invention has a protective and/or preventive effect on the infants or young children: it promotes and/or induces Community type B in the gut of the infants or young children fed with the nutritional composition of the present invention, and reduces Community C., in comparison to the respective communities in the gut of infants or young children fed predominantly or exclusively with a conventional nutritional composition not comprising said oligosaccharides (i.e. not comprising the at least one fucosylated oligosaccharide and the at least one N-acetylated oligosaccharide).

The major and surprising health benefit of the nutritional composition of the present invention is that it reduces the amount of antibiotics prescribed to the infants and young children. This is due to that specific taxa of the microbiota are changed.

In a particular aspect, the present invention also refers to a nutritional composition for use in preventing and/or treating infection in infants or young children.

By infection is meant pathological infection, i.e. typically does not refer to the colonization of the gut with bacteria but instead the situation where the infant or young child becomes ill due to the infection. Typically this will lead to fever in the infant or young child, and/or diarrhoea, coughing, or other symptoms. In pathological infections, a doctor may prescribe antibiotics.

The beneficial health benefits provided by the composition of the invention can be short term and/or long term effects.

The effect may be immediate with the administration of the composition of the present invention, or later in life, i.e. after the administration of the composition, e.g. from 1 week to several months, for example from 2 to 4 weeks, from 2 to 6 weeks, from 2 to 8 weeks, from 1 to 6 months or from 2 to 12 months after said administration.

Other Objects:

Another object of the present invention is the use of at least one fucosylated oligosaccharide and at least one N-acetylated oligosaccharide in the preparation of a nutritional composition for promoting Community type B and/or reducing Community type C in infants or young children, in comparison to the these communities in the gut of infants or young children fed predominantly or exclusively with a conventional nutritional composition not comprising said oligosaccharides.

Another object of the present invention is the use of the nutritional composition according to the present invention for promoting Community type B and/or reducing Community type C in infants or young children and thereby preventing and/or treating infection in infants or young children.

In another particular object of the present invention refers to a nutritional composition comprising at least one fucosylated oligosaccharide and at least one N-acetylated oligosaccharide, for use to promote Community type B and/or reduce Community type C in infants or young children, thereby preventing and/or treating diseases/conditions (e.g. infections, inflammations . . . ) involving fever and/or the administration of antibiotics or of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population etc.) also apply for this aspect.

Another object of the present invention is a pharmaceutical composition comprising at least one fucosylated oligosaccharide and at least one N-acetylated oligosaccharide for promoting Community type B and/or reducing Community type C in infants or young children in comparison to these communities in the gut of infants or young children fed predominantly or exclusively with a conventional nutritional composition not comprising said oligosaccharides.

This pharmaceutical composition may be used for preventing and/or treating infection in infants or young children.

Another object of the present invention refers to a method for promoting Community type B and/or reducing Community type C in infants or young children in the gut of infants or young children, in comparison to the global microbiota in the gut of infants or young children fed predominantly or exclusively with a conventional nutritional composition not comprising said oligosaccharides, said method comprising administering to said infant or young child a nutritional composition comprising at least one fucosylated oligosaccharide and at least one N-acetylated oligosaccharide.

Another object of the present invention is a method for preventing and/or treating infection infants or young children, said method comprising administering to said infant or young child a nutritional composition comprising at least one fucosylated oligosaccharide and at least one N-acetylated oligosaccharide.

The previously-mentioned embodiments and examples (e.g. related to the types and amounts of oligosaccharide, the nutritional composition, the administration, the targeted population . . . ) also apply for these various objects (i.e. uses, pharmaceutical composition, methods . . . ).

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EMBODIMENTS

The invention may be described in the following embodiments; each of those embodiment being combinable with the embodiments described above:

1. Nutritional composition comprising at least one fucosylated oligosaccharide and at least one N-acetylated oligosaccharide, for use to prevent and/or treat infection by promoting a Community B and/or to reducing a Community C in an infant or young child, wherein said promotion includes an up-regulation of the population of Bifidobacterium and said reduction includes a down-regulation of the populations of Escherichia and/or Peptostreptococcaceae, in comparison to the microbiota in the gut of infants or young children fed predominantly or exclusively with the conventional nutritional composition not comprising said oligosaccharides.
2. Nutritional composition according to embodiment 1, wherein the use is to prevent and/or treat infection later in life.
3. Nutritional composition for use according to any of the preceding embodiments wherein the fucosylated oligosaccharide is selected from the group consisting of the fucosylated oligosaccharide is selected from the list consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.
4. Nutritional composition according to embodiment 1, wherein the use is to prevent and/or treat infection later in life.
5. Nutritional composition for use according to any of the preceding embodiments wherein the fucosylated oligosaccharide(s) is/are in a total amount of 0.2- to 2.2 g/L of the composition and/or in a total amount of 0.15-1.75 g/100 g of composition on a dry weight basis; and the N-acetylated oligosaccharide(s) is/are in a total amount of 0.05-0.85 g/L of the composition and/or in a total amount of 0.04-0.59 g/100 g of composition on a dry weight basis.
6. Nutritional composition according to any of the preceding embodiments, wherein the fucosylated oligosaccharide comprises a 2' fucosyl-epitope.
7. Nutritional composition according to any one of the preceding embodiments, wherein the fucosylated oligosaccharide is 2'-fucosyllactose (2'FL).
8. Nutritional composition according to any one of the preceding embodiments, wherein the N-acetylated oligosaccharide is lacto-N-tetraose (LNT), lacto-N-neotetraose (LNnT) or any combination thereof.
9. Nutritional composition according to any one of the preceding embodiments, wherein the N-acetylated oligosaccharide is lacto-N-neotetraose (LNnT), para-lacto-N-neohexaose (para-LNnH) or any combination thereof, preferably wherein the N-acetylated oligosaccharide is lacto-N-neotetraose (LNnT).
10. Nutritional composition according to any one of the preceding embodiments, comprising 2'-fucosyllactose and lacto-N-neotetraose (LNnT), or comprising an oligosaccharide mixture consisting of 2'-fucosyllactose (2'FL) and lacto-N-neotetraose (LNnT).
11. Nutritional composition according to any one of the preceding embodiments, wherein the fucosylated oligosaccharide(s) is/are in a total amount of 0.8-1.5 g/L of the composition and/or in a total amount of 0.62-1.16 g/100 g of composition on a dry weight basis; and/or the N-acetylated oligosaccharide(s) is/are in a total amount of 0.5-0.8 g/L of the composition and/or in a total amount of 0.39-0.62 g/100 g of composition on a dry weight basis.
12. Nutritional composition according to any one of the preceding embodiments, comprising at least another oligosaccharide(s) and/or fiber(s) and/or precursor(s) thereof selected from the list comprising galacto-oligosaccharides (GOS), fructo-oligosaccharides (FOS), xylooligosaccharides (XOS), inulin, polydextrose, sialylated oligosaccharides, sialic acid, fucose and any combination thereof.
13. Nutritional composition according to any one of the preceding embodiments, said composition further comprising at least one probiotic in an amount of from $10^3$ to $10^{12}$ cfu/g of said composition (dry weight).
14. Nutritional composition according to any one of the preceding embodiments, wherein said nutritional composition is an infant formula, a starter infant formula, a follow-on or follow-up infant formula, a preterm formula, a baby food, an infant cereal composition, a fortifier or a supplement.

15. Nutritional composition according to of any one of the preceding embodiments for infants under 6 months of age.

16. Nutritional composition according to any one of the preceding embodiments, wherein said infant or young child is selected from the group consisting of preterm infants, infants born by Caesarean-section, infants born small for gestational age or with low birth weight, hospitalized infants/young children, infants/young children treated or having been treated by antibiotics and/or infants/young children suffering or having suffered from gut infection and/or gut inflammation.

17. Nutritional composition according to any one of the preceding embodiments, for use in reducing fever and/or in reducing the use of antibiotics and/or in reducing the use of antipyretics in the infant or young child.

18. Nutritional composition comprising at least one fucosylated oligosaccharide and at least one N-acetylated oligosaccharide, for use in reducing fever and/or in reducing the administration of antipyretics in an infant or a young child, wherein the fucosylated oligosaccharide(s) is/are in a total amount of 0.2- to 2.2 g/L of the composition and/or in a total amount of 0.15-1.75 g/100 g of composition on a dry weight basis; and the N-acetylated oligosaccharide(s) is/are in a total amount of 0.05-0.85 g/L of the composition and/or in a total amount of 0.04-0.59 g/100 g of composition on a dry weight basis.

19. Nutritional composition comprising at least one fucosylated oligosaccharide and at least one N-acetylated oligosaccharide, for use in reducing the administration of antibiotics in an infant or a young child, wherein the fucosylated oligosaccharide(s) is/are in a total amount of 0.2- to 2.2 g/L of the composition and/or in a total amount of 0.15-1.75 g/100 g of composition on a dry weight basis; and the N-acetylated oligosaccharide(s) is/are in a total amount of 0.05-0.85 g/L of the composition and/or in a total amount of 0.04-0.59 g/100 g of composition on a dry weight basis.

20. Nutritional composition comprising at least one fucosylated oligosaccharide and at least one N-acetylated oligosaccharide, for use in preventing and/or treating diseases/conditions involving fever and/or the administration of antibiotics and/or the administration of antipyretics in an infant or a young child, wherein the fucosylated oligosaccharide(s) is/are in a total amount of 0.2- to 2.2 g/L of the composition and/or in a total amount of 0.15-1.75 g/100 g of composition on a dry weight basis; and the N-acetylated oligosaccharide(s) is/are in a total amount of 0.05-0.85 g/L of the composition and/or in a total amount of 0.04-0.59 g/100 g of composition on a dry weight basis.

21. Use of a nutritional composition comprising at least one fucosylated oligosaccharide and at least one N-acetylated oligosaccharide for reducing fever and/or for reducing the administration of antibiotics and/or of antipyretics in an infant or a young child, wherein the fucosylated oligosaccharide(s) is/are in a total amount of 0.2- to 2.2 g/L of the composition and/or in a total amount of 0.15-1.75 g/100 g of composition on a dry weight basis; and the N-acetylated oligosaccharide(s) is/are in a total amount of 0.05-0.85 g/L of the composition and/or in a total amount of 0.04-0.59 g/100 g of composition on a dry weight basis.

22. A method of preventing and/or treating an infection in an infant or young child, by providing a nutritional composition according to any one of the preceding embodiments 1 to 20.

EXAMPLES

Background and aims: HMOs may provide health benefits to infants partly by shaping the development of the intestinal microbiota. We explored stool microbiota in relation to reported morbidity and medication use in infants fed formula supplemented with 2 HMOs.

Example 1

An example of the composition of a nutritional composition (e.g. an infant formula) according to the present invention is given in the below table 1. This composition is given by way of illustration only.

TABLE 1

Example of the composition of a nutritional composition (e.g. an infant formula)

| Nutrients | | per 100 kcal | per liter |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (μg) | | 8 | 50 |
| Se (μg) | | 2 | 13 |
| Vitamin A (μg RE) | | 105 | 700 |
| Vitamin D (μg) | | 1.5 | 10 |
| Vitamin E (mg TE) | | 0.8 | 5.4 |
| Vitamin K1 (μg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (μg) | | 9 | 60 |
| Pantothenic acid (mg) | | 0.45 | 3 |
| Vitamin B12 (μg) | | 0.3 | 2 |
| Biotin (μg) | | 2.2 | 15 |
| Choline (mg) | | 10 | 67 |
| Fe (mg) | | 1.2 | 8 |
| I (μg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Example 2

Description of the Clinical Study

A safety trial was conducted at the Dipartimento Materno Infantile, UnitA Operativa Complessa di Neonatologia e Terapia Intensiva Neonatale, AOUP "Paolo Giaccone" in Palermo, Italy and Kinderartsenpraktijk in Hasselt, Belgium.

This study was a randomized, controlled, two-center interventional clinical trial of 2 parallel formula-fed groups. The study population for the formula-fed groups consisted of healthy, full-term male and female infants old 0 to 14 days at enrolment who were exclusively formula-fed at the time of enrolment. Eligible infants were randomly assigned to one of two study formulas (Control or Test) using delivery method (vaginal or Caesarean section) and gender as stratification factors. For Stage 1, randomized infants received exclusive feedings with the Test or Control formulas from enrolment through 4 months of age in amounts suitable for their weight, age and appetite. Parents/caregivers, investigators, study support staff, and the Clinical Project Manager were blinded to the identity of the study formulas.

The infant formulas used in the study were as follows:
A Control Formula was given to the Control group: it was a standard whey-predominant starter infant formula comprising LC-PUFA and without probiotics (66.9 kcal/100 ml reconstituted formula, 1.889 g protein/100 kcal powder with a whey:casein ratio of 71.6%:28.4%, see table 2 for the detailed composition).
Test Formula was given to the Test group: it was the Control Formula except that a part of lactose has been replaced with 2 HMOs (2FL and LNnT) in the following amounts 0.5-0.6 g LNnT and 1.0-1.2 g 2'FL per liter of reconstituted formula (see table 2 for the detailed composition).

As reference group (Breast-fed group=BF group), at least for 3 months exclusively breast-fed infants were recruited for stool sampling at 3 months of age.

TABLE 2

Composition of the Control Formula and the Test Fomula

| Parameter | 100 g Control formula | 100 g Test formula |
|---|---|---|
| Energy (kcal) | 518.7 | 518.7 |
| Water (g) | 2.6 | 2.6 |
| Fat (g) | 27.5 | 27.5 |
| Fatty acids saturated (g) | 11 | 11 |
| Fatty acids Mono-unsaturated (g) | 9.4 | 9.4 |
| Alpha-Linolenic Acid C18:3 n-3 (mg) | 510 | 510 |
| Docosahexaenoic Acid C22:6 n-3 (DHA) (mg) | 61 | 61 |
| Arachidonic Acid C20:4 n-6 (ARA) (mg) | 61 | 61 |
| Linoleic Acid C18:2 n-6 (mg) | 4270 | 4270 |
| Fatty acids Poly-unsaturated (g) | 4.9 | 4.9 |
| Protein (g) | 9.8 | 9.8 |
| Available Carbohydrates (g) | 58 | 58 |
| Lactose (g) | 56 | 55 |
| HMOs    LNnT(g) | 0 | 0.39-0.47 |
|    2FL (g | 0 | 0.77-0.93 |
| Sugars (g) | 56 | 56 |
| Ash (g) | 2.1 | 2.1 |
| Sodium (mg) | 162 | 162 |
| Potassium (mg) | 575 | 575 |
| Chloride (mg) | 348 | 348 |
| Calcium (mg) | 317 | 317 |
| Phosphorus (mg) | 178 | 178 |
| Magnesium (mg) | 43 | 43 |
| Manganese (μg) | 121 | 121 |
| Selenium (μg) | 13 | 13 |
| Iron (mg) | 4.8 | 4.8 |
| Copper (mg) | 0.37 | 0.37 |
| Zinc (mg) | 5 | 5 |
| Iodine (μg) | 102 | 102 |
| Fluoride (μg) | 60 | 60 |
| Vitamin A (Retinol) (μg RE) | 542 | 542 |
| Vitamin D (Calciferol) (μg D) | 7.6 | 7.6 |
| Vitamin E (Tocopherol) (mg TE) | 8.4 | 8.4 |
| Vitamin K (Phytoquinone) (μg) | 45 | 45 |
| Vitamin C (Ascorbic Acid) (mg) | 80 | 80 |
| Vitamin B1 (Thiamin Base) (mg) | 0.6 | 0.6 |
| Vitamin B2 (Riboflavin) (mg) | 0.67 | 0.67 |
| Niacin (mg) | 4.1 | 4.1 |
| Vitamin B6 (Pyridoxine Base) (mg) | 0.34 | 0.34 |
| Folic acid (μg) | 80.9 | 80.9 |
| Pantothenic Acid (mg) | 3.4 | 3.4 |
| Vitamin B12 (Cyanocobalamin) (μg) | 1.8 | 1.8 |
| Biotin (μg) | 14 | 14 |
| Choline (mg) | 48 | 48 |
| Inositol (mg) | 48 | 48 |
| Taurine (mg) | 33 | 33 |
| Carnitine, L-(mg) | 9.5 | 9.5 |
| Nucleotides (mg) | 15 | 15 |
| Adenosine 5'-Monophosphate (mg) | 3.8 | 3.8 |
| Cytidine 5'-Monophosphate (mg) | 6 | 6 |
| Guanosine 5'-Monophosphate (mg) | 1.2 | 1.2 |
| Uridine 5'-Monophosphate (mg) | 4 | 4 |
| Ca/P (ratio) | 1.781 | 1.781 |
| Linoleic/Alpha-linolenic (ratio) | 8.373 | 8.373 |
| Vitamin C/Fe (ratio) | 16.667 | 16.667 |
| Phenylalanine, L-(mg) | 488 | 488 |
| Alanine, L-(mg) | 391 | 391 |
| Arginine, L-(mg) | 258 | 258 |
| Cystine, L-(mg) | 247 | 247 |
| Histidine, L-(mg) | 226 | 226 |
| Isoleucine, L-(mg) | 502 | 502 |
| Leucine, L-(mg) | 1045 | 1045 |
| Methionine, L-(mg) | 205 | 205 |
| Threonine, L-(mg) | 460 | 460 |
| Tryptophan, L-(mg) | 200 | 200 |
| Tyrosine, L-(mg) | 399 | 399 |
| Valine, L-(mg) | 542 | 542 |

Evaluation of stool microbiota were made for each group at 3 months of age and using different techniques, see Table 3.

TABLE 3

Overview of samples

| No of samples | ITT | PP | PP samples 16S rDNA |
|---|---|---|---|
| Control | 87 | 75 | 63 |
| Test | 88 | 71 | 58 |
| Breast-Fed | — | 38 | 33 |

Table 3 gives an overview of the samples. Number of infants in the intention to treat groups (ITT), per protocol groups (PP) and number of stool samples that were available from the per protocol groups or the breastfed reference group for microbiota analysis by global 16S rDNA sequencing.

Materials and Methods

Stool Collection

Stool samples were collected by parents from all subjects at home and within the 48 hours preceding the 3-month visit. To this end parents were supplied a kit (insulated bag, ice pack, spatula pots, sealable plastic bags, instruction sheet). Parents were asked to collect 2 samples, to store the samples at home in a −20° C. freezer and to transport the stool samples within the insulated bag containing a frozen ice pack to the site of the visit where samples were kept frozen at −80° C. Samples were then shipped to the Nestle Research Center, Switzerland, on dry ice and kept frozen at −80° C. until analysis.

Fecal DNA Extraction

Total DNA was extracted using the QIAamp DNA Stool Mini Kit (QIAGEN), following the manufacturer's instructions, except for the addition of a series of mechanical disruption steps (11×45 s) using a FastPrep apparatus and Lysing Matrix B tubes (MP Biochemicals) (Junick and Blaut, 2012, Quantification of human fecal *bifidobacterium* species by use of quantitative real-time PCR analysis targeting the groEL gene. Appl Environ Microbiol 78: 2613-2622).

Amplification of 16S Genes and Sequencing

Then, the 16S variable region V3 to V4 were PCR amplified using universal (Klindworth et al., 2013, Evaluation of general 16S ribosomal RNA gene PCR primers for classical and next-generation sequencing-based diversity studies. Nucleic Acids Res 41: e1) and sequenced with Illumina Miseq technology as previously described (Caporaso et al., 2012, Ultra-high-throughput microbial community analysis on the Illumina HiSeq and MiSeq platforms. ISME J 6: 1621-1624).

16S Data Analysis

After quality filtering, 6'710'039 sequences described the microbiota of 154 samples of the per protocol (PP) set (see Table 3), with an average coverage of 42739 sequences per sample classified in 173 OTUs. Three samples with less than 10'000 sequences were excluded from the 16S rDNA analysis.

Raw sequence data were analyzed using a blend of Mothur (Schloss et al., 2009, Introducing mothur: open-source, platform-independent, community-supported software for describing and comparing microbial communities. Appl Environ Microbiol 75: 7537-7541) and QIIME (Caporaso et al., 2010, QIIME allows analysis of high-throughput community sequencing data. Nat Methods 7: 335-336) software packages. Paired-end sequences were demultiplexed and joined as described (Kozich et al., 2013 Development of a dual-index sequencing strategy and curation pipeline for analyzing amplicon sequence data on the MiSeq Illumina sequencing platform. Appl Environ Microbiol 79: 5112-5120). Then, sequences were splitted in separated fasta files for each sample using Mothur commands [deunique.seqs( ), degap.seqs( ), and split.groups( )]. Conversion to QIIME format using add_qiime_labels.py and subsequent analytical steps were performed in QIIME. Chimera check and OTUs picking at 97% identity were performed using Uchime (Edgar et al., 2011, UCHIME improves sensitivity and speed of chimera detection. Bioinformatics 27: 2194-2200) with pick_open_reference.py. Taxonomy assignment was performed on representative sequences using RDP Classifier with confidence threshold of 0.6 (Wang et al., 2007, Naive Bayesian classifier for rapid assignment of rRNA sequences into the new bacterial taxonomy. Appl Environ Microbiol 73: 5261-5267). OTU representative sequences were aligned using PyNast method (Caporaso et al., 2010, PyNAST: a flexible tool for aligning sequences to a template alignment. Bioinformatics 26: 266-267) and Uclust as pairwise alignment method. The resulting multiple alignments was then filtered and used to build a phylogenetic tree with the FastTree method (Price et al., 2009, FastTree: computing large minimum evolution trees with profiles instead of a distance matrix. Mol Biol Evol 26: 1641-1650). After quality filtering (Bokulich et al., 2013, Quality-filtering vastly improves diversity estimates from Illumina amplicon sequencing. Nat Methods 10: 57-59), diversity analyses were performed in QIIME, mother, and at genus level with the websites Calypso at http://bioinfo.qimr.edu.au/calypso.

Results

Healthy term infants <14 days old were randomly assigned to infant formula (Control) or the same formula with 1.0 g/L 2'Fucosyllactose and 0.5 g/L Lacto-N-neotetraose (Test) from enrolment to 6 months; all infants received the same follow-up formula without HMOs from 6-12 months. Breastfed infants (BF) served as a reference group. Stool microbiota of each infant at 3 months and 12 months was analyzed by 16S rDNA sequencing. Community types were defined based on these microbiota composition profiles using Dirichlet multinomial mixtures (DMM) modelling framework (see Holmes I, Harris K, Quince C (2012) Dirichlet Multinomial Mixtures: Generative Models for Microbial Metagenomics. PLoS ONE 7(2): e30126. doi: 10.1371/journal.pone.0030126). With this probabilistic modelling approach, each sample is associated to a faecal community type (Community Type) at genus level. It is an unsupervised approach which does not take into account the origin (in this case, which treatment group) of the samples. The optimal number of community types and their taxonomic composition depend on the full dataset of microbiota composition profiles and are defined by the DMM.

After clustering into community types, the distribution of said types was compared between the treatment groups.

Communities A, B and C were only observed in samples from infants 3 months of age, whereas communities D, E, F and G were essentially only observed in samples from 12 month old infants.

At 3 months, microbiota composition in the Test group (n=58, fed with HMOS composition) appeared closer to the breast fed group (BF, n=35) than the Control group (fed with infant formula conventional composition, n=62), with respect to the distribution of microbiota community types (A, B, or C). HMOS supplementation decreased the number of infants with the C community, which community is specific to formula-fed infants. At the same time HMOS supplementation increased the number of infants with the B-community, which community is the most frequent in breast-fed infants.

Their associations with formula supplementation and with reported morbidities identified a priori and medication use through 12 months were analyzed using chi-2-tests.

The data lead us to conclude that infant formula with HMOs shifted microbiota towards that of breastfed infants. The reduced likelihood of medication use with HMOs is believed to be linked to gut microbiota community types.

The grouping of microbiota to community types is shown in FIG. 1.

TABLE 2

Distribution of fecal community types in treatment groups

| | 3 months | | | 12 months | | |
|---|---|---|---|---|---|---|
| | BF | TEST | CONTROL | BF | TEST | CONTROL |
| A | 0 | 0 | 0 | 11 | 10 | 10 |
| B | 0 | 0 | 0 | 21 | 22 | 7 |
| C | 0 | 0 | 0 | 1 | 26 | 45 |
| D | 9 | 19 | 23 | 2 | 0 | 0 |

TABLE 2-continued

Distribution of fecal community types in treatment groups

|   | 3 months | | | 12 months | | |
|---|---|---|---|---|---|---|
|   | BF | TEST | CONTROL | BF | TEST | CONTROL |
| E | 6 | 10 | 11 | 0 | 0 | 0 |
| F | 2 | 1 | 5 | 0 | 0 | 0 |
| G | 13 | 16 | 10 | 0 | 0 | 1 |

Figure 2:
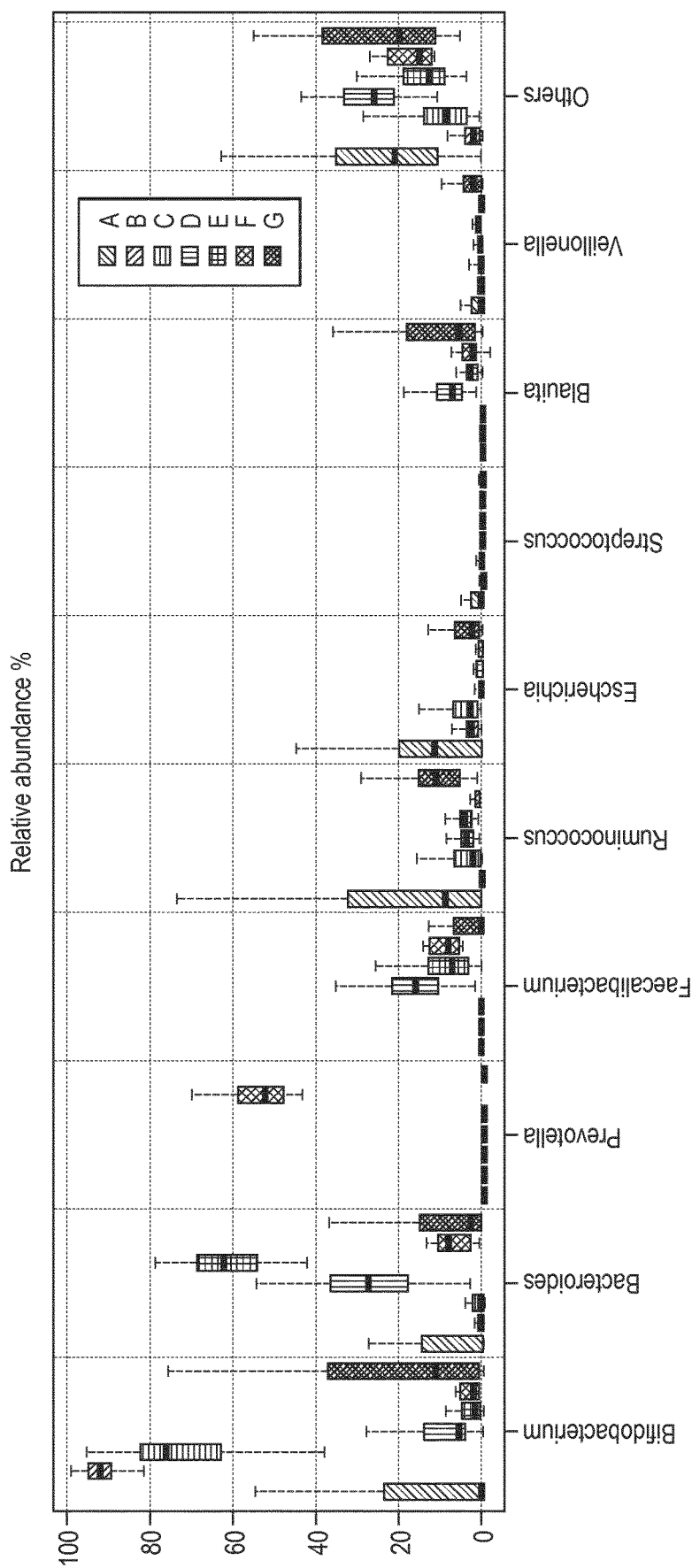
FIG. 2 shows the distribution of the taxa at genus level in the samples of seven community types defined in our study.

See also FIG. 2.

The distribution of community types B and C are significantly different in the groups.

TABLE 3

Frequency and column percentages of community types by feeding group at 3 months

| | Counts | | | p-values | | | % | | |
|---|---|---|---|---|---|---|---|---|---|
| | | | | TEST vs | TEST vs | BF vs | | | |
| Community | BF | CTRL | TEST | CTRL | BF | CTRL | BF | CTRL | TEST |
| G | 0 | 1 | 0 | 1.00000 | 1.00000 | 1.00000 | 0 | 2 | 0 |
| A | 11 | 10 | 10 | 1.00000 | 0.13071 | 0.11771 | 31 | 16 | 17 |
| B | 21 | 7 | 22 | 0.00140 | 0.05651 | <2e−16 | 60 | 11 | 38 |
| C | 1 | 44 | 26 | 0.00450 | <2e−16 | <2e−16 | 3 | 71 | 45 |
| D | 2 | 0 | 0 | 1.00000 | 0.13891 | 0.13331 | 6 | 0 | 0 |

BF = breast fed group; CTRL = control group (infant formula without HMOS supplementation); TEST = test group (infant formula supplemented with HMOS).

Table 3 shows the results the likelihood of cumulative reported antibiotic use through 12 months. This was increased in infants harbouring the C community, and decreased in infants with the B community.

TABLE 4A

Antibiotics use at 4 months

| | Antibiotics cumulative 4 M | | | | | |
|---|---|---|---|---|---|---|
| | No | (%) | Yes | (%) | Total | (%) | p-value |
| | | | Communtiy at 3 M | | | | |
| G | 1 | 100.0 | 0 | 0.0 | 1 | 100 | 1.000 |
| A | 15 | 75.0 | 5 | 25.0 | 20 | 100 | 0.435 |
| B | 21 | 72.4 | 8 | 27.6 | 29 | 100 | 0.369 |
| C | 41 | 58.6 | 29 | 41.4 | 70 | 100 | 0.117 |
| TOTAL | 78 | 65.0 | 42 | 35.0 | 120 | 100 | 0.092 |

Figure 3:
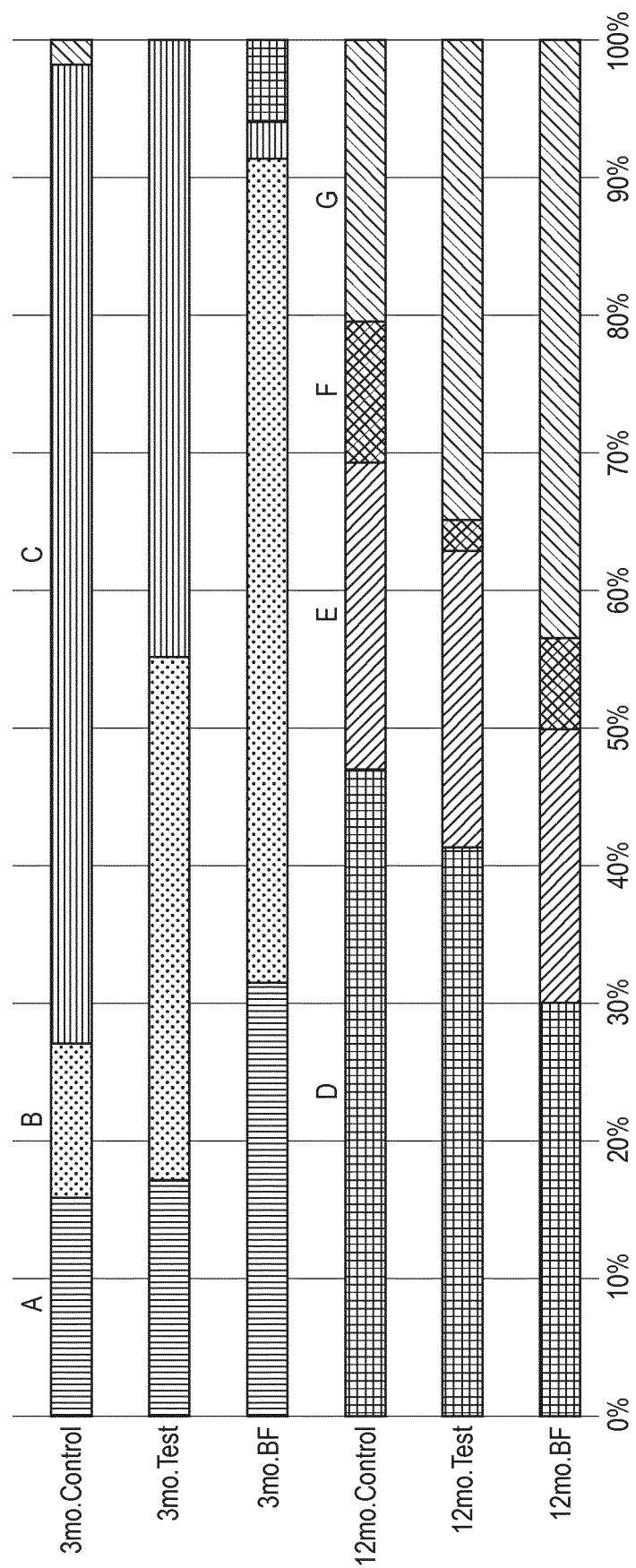
FIG. 3 shows the distribution of the microbiota communities within the different groups of subjects.

The data from table 4A is also represented in FIG. 3A.

TABLE 4B

Antibiotics use at 6 months

| | Antibiotics cumulative 6 M | | | | | |
|---|---|---|---|---|---|---|
| | No | (%) | Yes | (%) | Total | (%) | p-value |
| | | | Community at 3 M | | | | |
| G | 1 | 100.0 | 0 | 0.0 | 1 | 100 | 1.000 |
| A | 13 | 65.0 | 7 | 35.0 | 20 | 100 | 0.461 |
| B | 19 | 65.5 | 10 | 34.5 | 29 | 100 | 0.209 |
| C | 33 | 47.1 | 37 | 52.9 | 70 | 100 | 0.064 |
| TOTAL | 66 | 55.0 | 54 | 45.0 | 120 | 100 | 0.064 |

Figure 4:
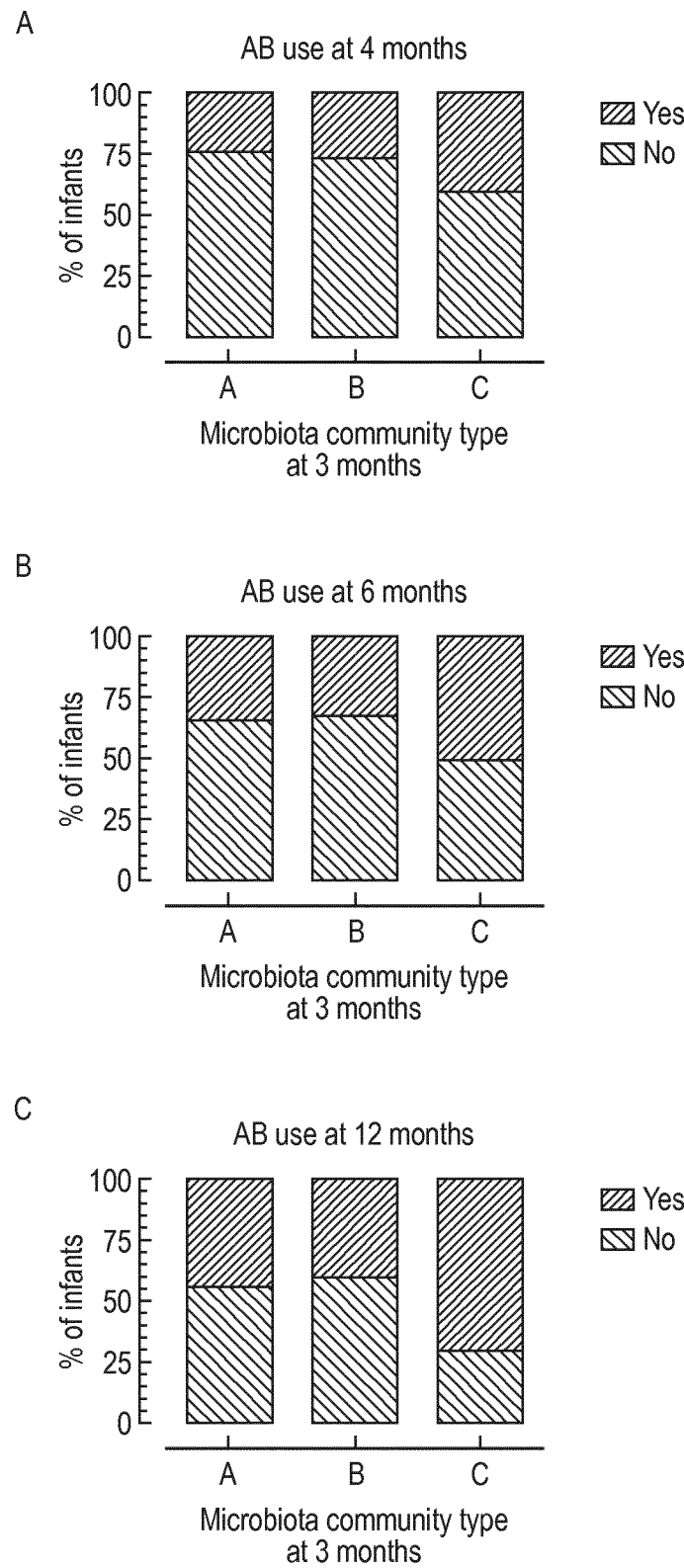
FIG. 4 shows the cumulative use of antibiotics in infants with different microbiota communities. See also Examples and Table 4.
Figure 5:
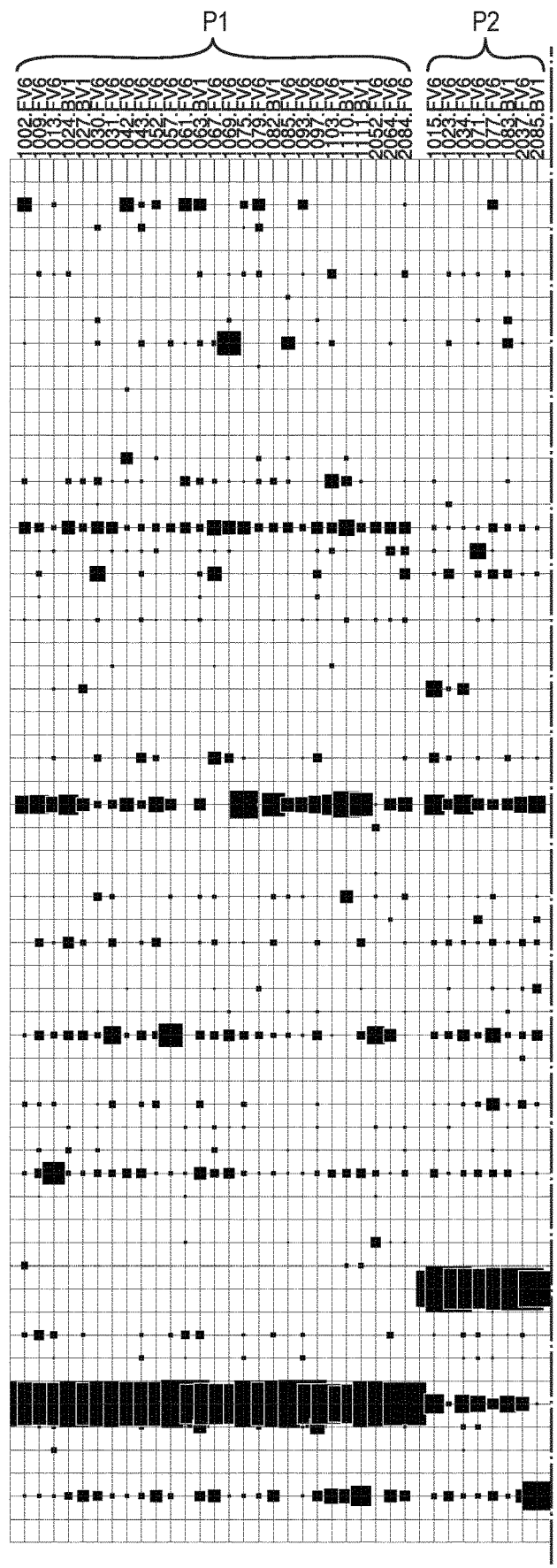
FIG. 5 shows an overview of the clusters of microbiota profiles from samples into community types. Samples are depicted by horizontal lines and taxa on vertical lines, with squares representing their relative amount in each sample (scale at bottom right). The numbers refer to community types.
Figure 5:
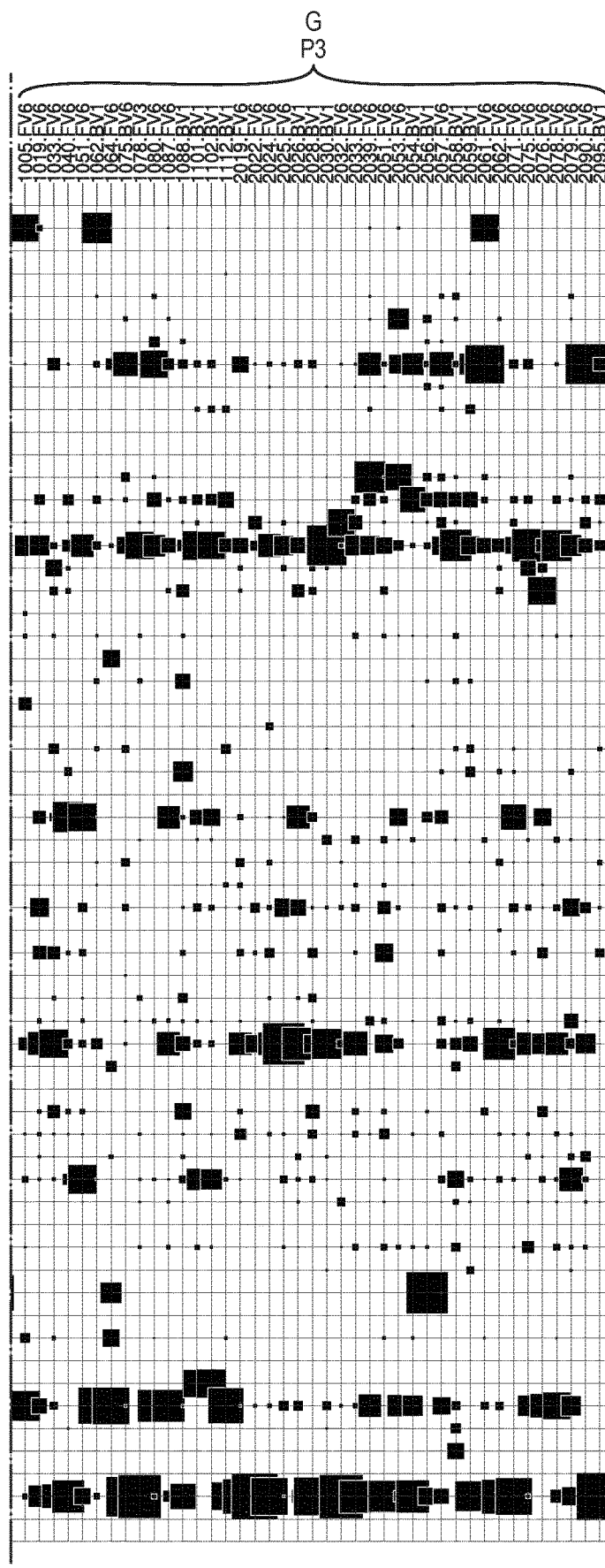
Figure 5:
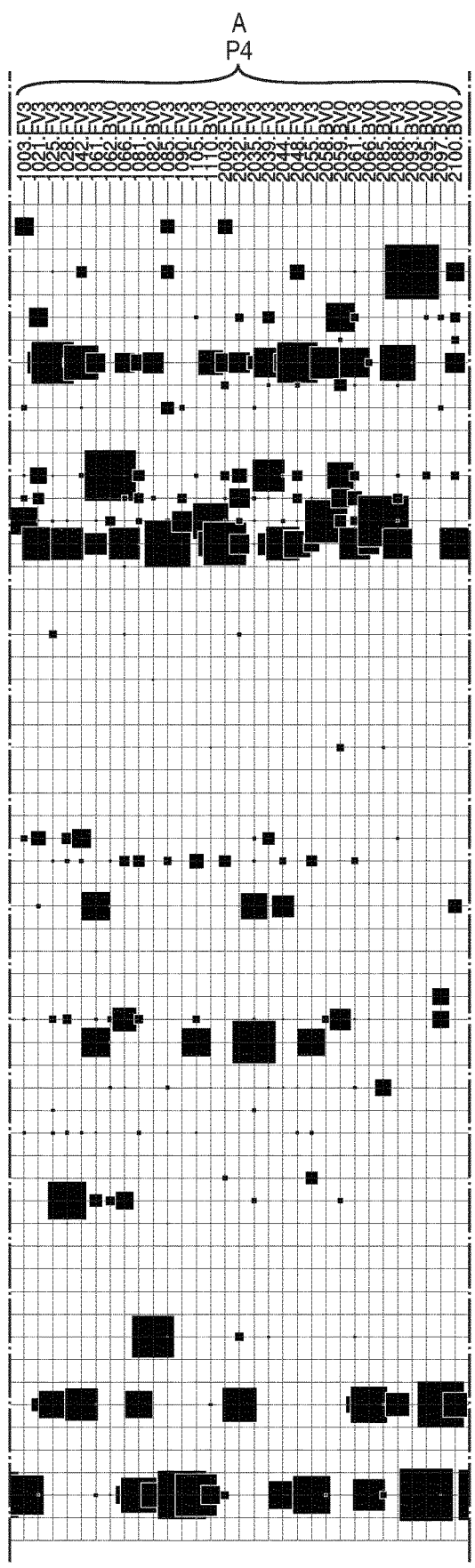
Figure 5:
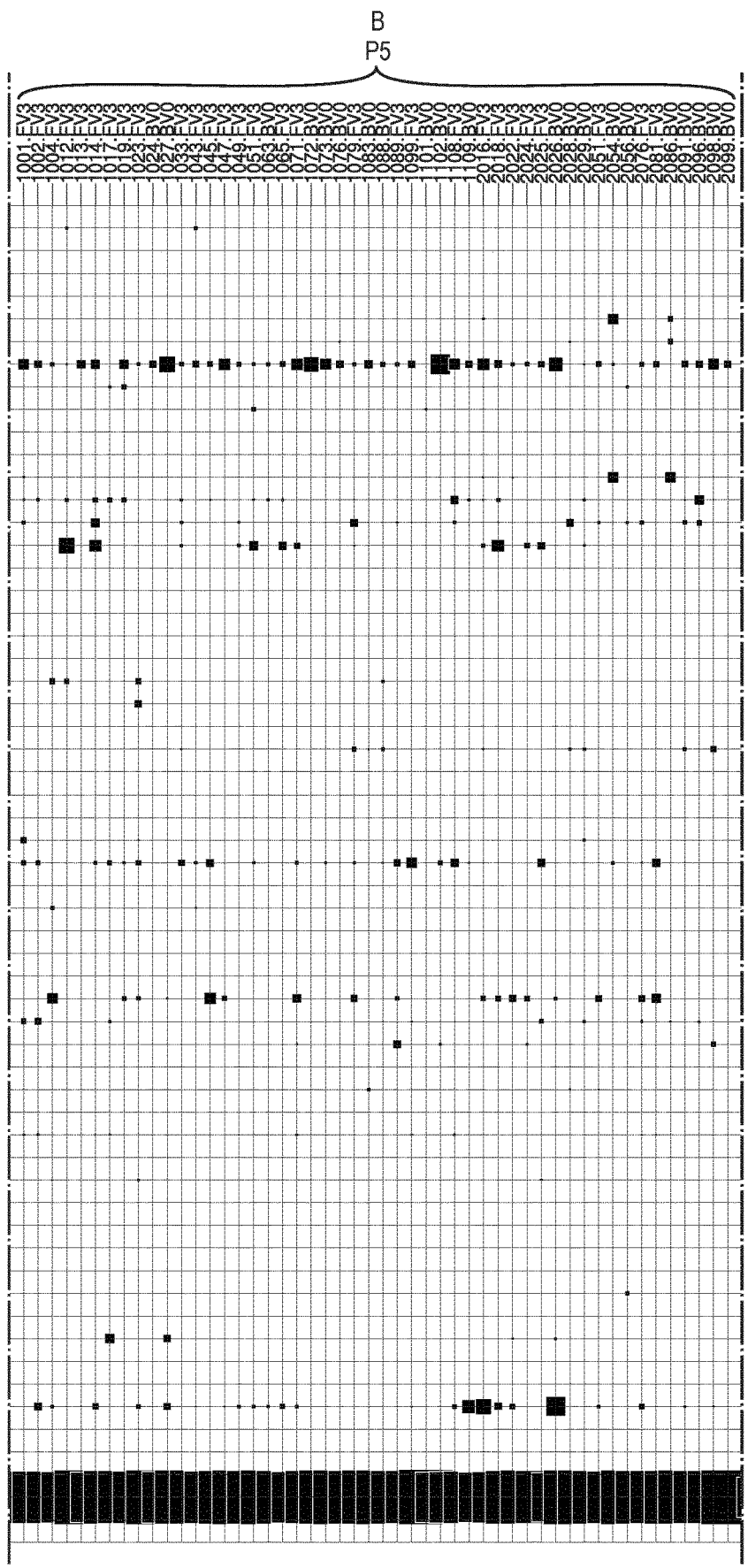
Figure 5:
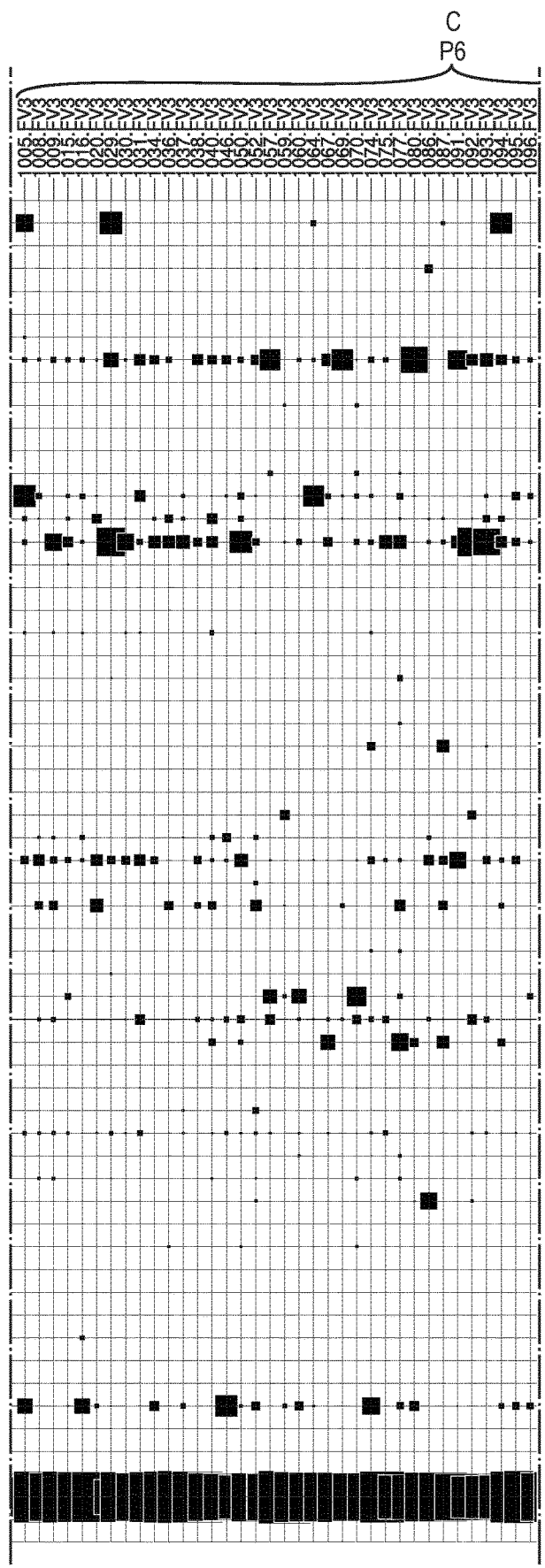
Figure 5:
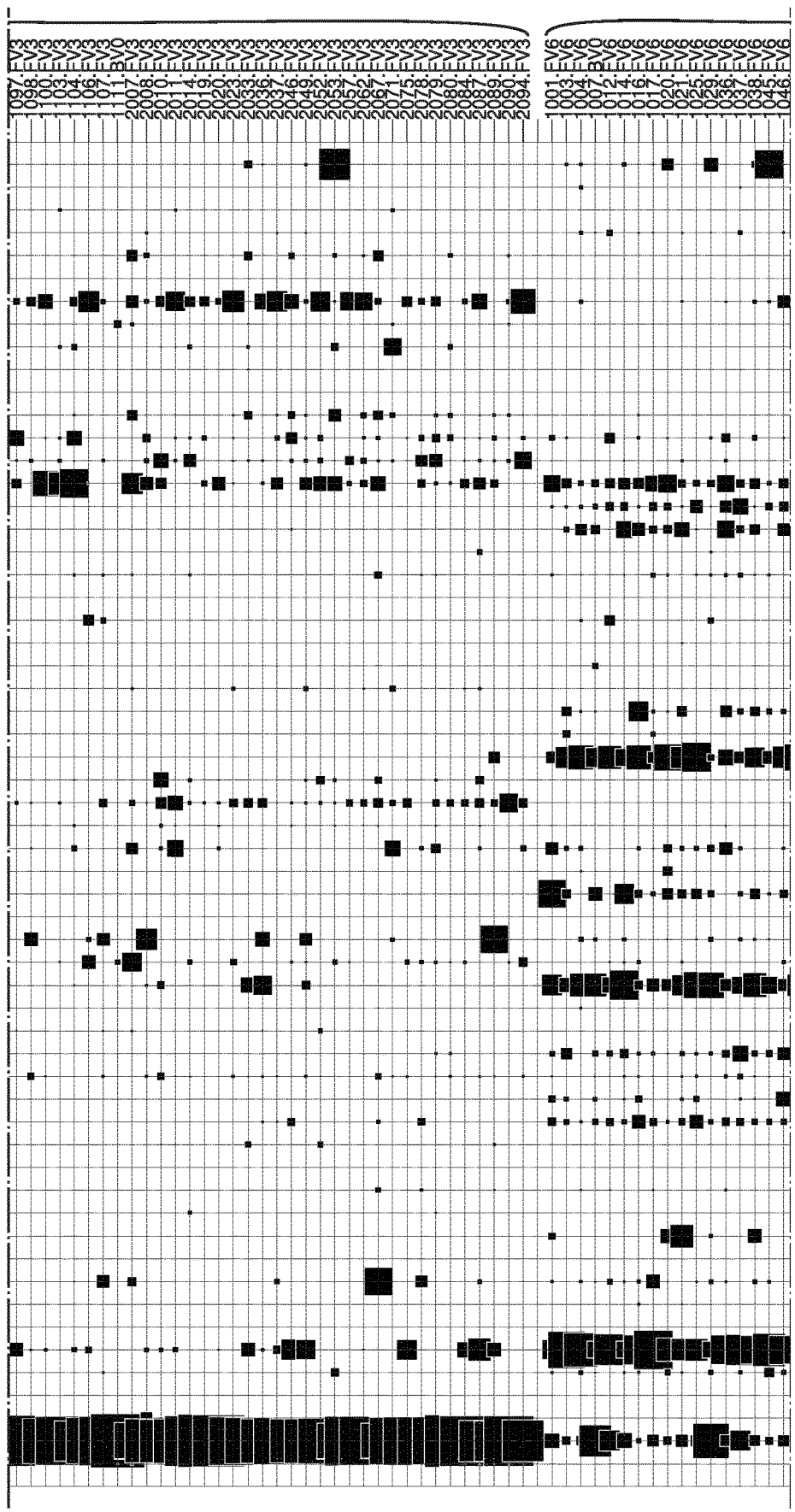
Figure 5:
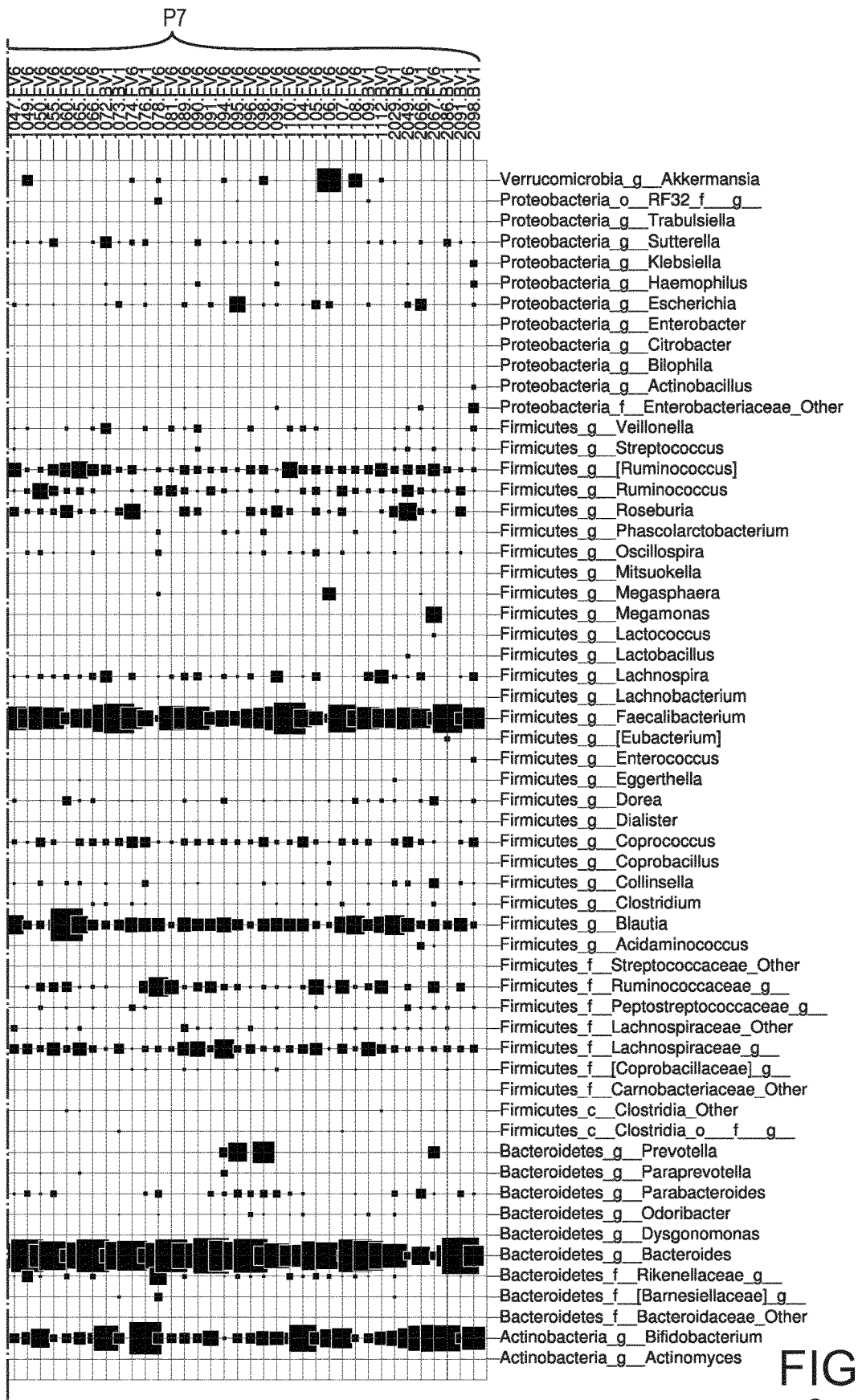
Figure 6:
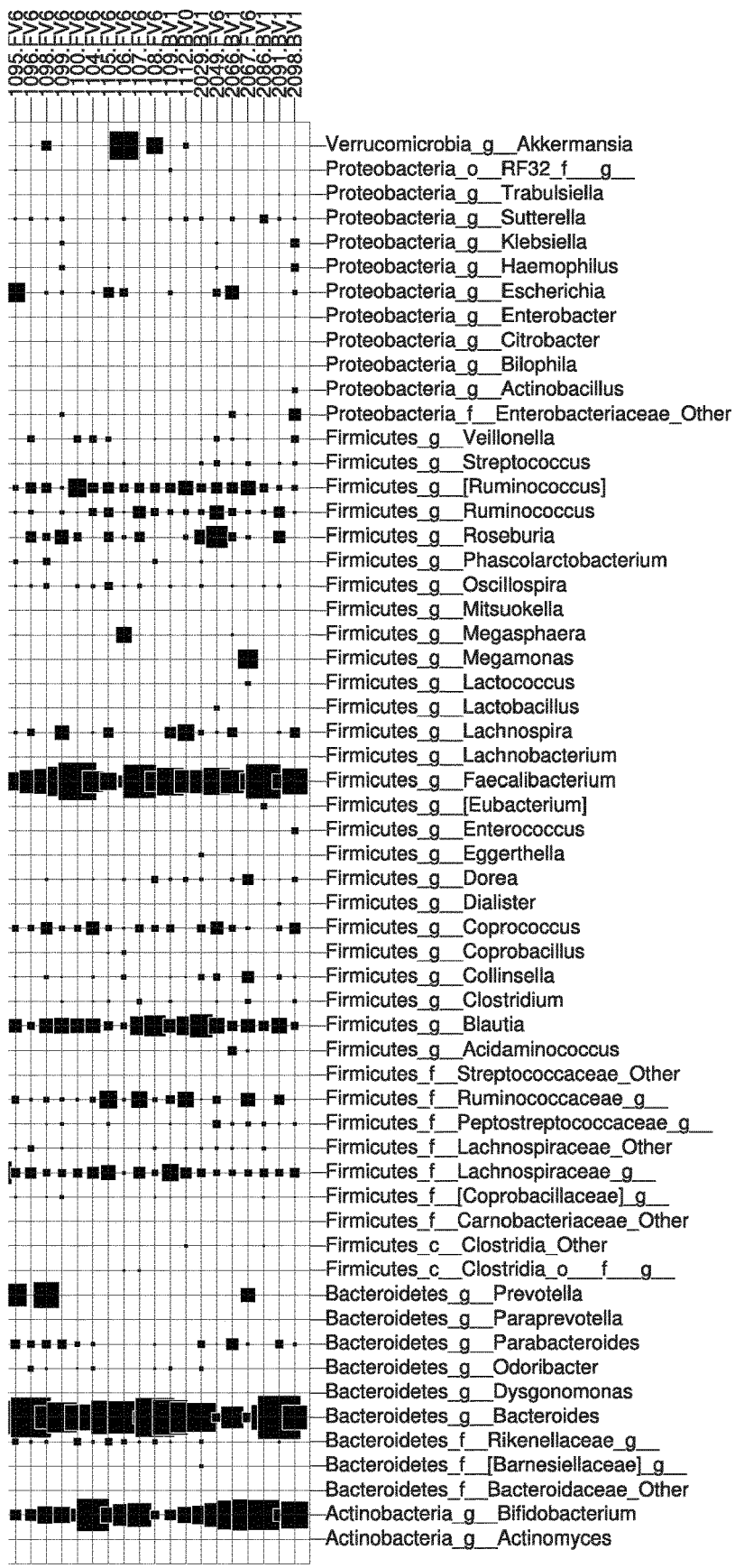
FIG. 6 shows an enlargement of a part of FIG. 5, to render the text legible.

The data from table 4B is also represented in FIG. 4B.

TABLE 4C

Antibiotics cumulative 12 M

| | No | (%) | Yes | (%) | Total | (%) | p-value |
|---|---|---|---|---|---|---|---|
| | | | Community at 3 M | | | | |
| G | 1 | 100.0 | 0 | 0.0 | 1 | 100 | 0.406 |
| A | 11 | 55.0 | 9 | 45.0 | 20 | 100 | 0.212 |
| B | 17 | 58.6 | 12 | 41.4 | 29 | 100 | 0.034 |
| C | 20 | 28.6 | 50 | 71.4 | 70 | 100 | 0.002 |
| TOTAL | 49 | 40.8 | 71 | 59.2 | 120 | 100 | 0.003 |

The data from table 4C is also represented in FIG. 4C.

Infants with microbiota Community type B have a lower risk of requiring antibiotics in the first year of life (12 M). Infants with microbiota Community type C have increased risk to require an For antibiotic use until 4 months and 6 months there was no statistical significance evident. However, based on the numbers one can discern a trend in the same direction. Infants with a microbiota Community type B have a lower risk Likelihood of cumulative reported antibiotic use through 12 months was increased in infants harbouring the C-community and decreased in babies with the B-community.

Thus, the present invention promotes Community B, and reduces Community C.

The invention claimed is:

1. A method to reduce or decrease an incidence of and/or treat infection by promoting a Community type B and/or by reducing a Community type C in an infant or young child in need thereof, wherein the Community type B is defined as a microbiota community comprising greater than 80% Bifidobactera (% relative abundance), and the Community type C is defined as a microbiota community comprising from 50 to 80% Bifidobacteria (% relative abundance) and further comprising one or more of Firmicutes, Bacteroidetes and/or Proteobacteria, the method comprising:
   administering a nutritional composition comprising at least one fucosylated oligosaccharide and at least one N-acetylated oligosaccharide to the infant or young child,
   wherein the at least one fucosylated oligosaccharide is in a total amount of 0.8-1.5 g/L of the nutritional composition and/or in a total amount of 0.62-1.16 g/100 g of the nutritional composition on a dry weight basis; and/or the at least one N-acetylated oligosaccharide is in a total amount of 0.5-0.8 g/L of the nutritional composition and/or in a total amount of 0.39-0.62 g/100 g of the nutritional composition on a dry weight basis, wherein the infant or young child is being treated by antibiotic and/or has been treated by antibiotic, and wherein the promoting of the Community type B and/or the reducing of the Community type C is in comparison to microbiota in the gut of infants or young children fed predominantly or exclusively with a conventional nutritional composition not comprising the at least one fucosylated oligosaccharide and the at least one N-acetylated oligosaccharide, wherein the nutritional composition reduces or decreases an incidence of and/or treats infection 2 weeks to 12 months after termination of the administering of the nutritional composition.

2. The method according to claim 1, wherein the at least one fucosylated oligosaccharide is selected from the group consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.

3. The method according to claim 1, wherein the at least one fucosylated oligosaccharide comprises 2'-fucosyllactose, and the at least one N-acetylated oligosaccharide comprises lacto-N-neotetraose (LNnT).

4. The method according to claim 1, wherein the nutritional composition is in a form selected from the group consisting of an infant formula, a starter infant formula, a follow-on or follow-up infant formula, a preterm formula, a baby food, an infant cereal composition, a fortifier and a supplement.

5. The method according to claim 1, wherein the infant or young child is under 6 months of age.

6. The method according to claim 1, wherein the infant or young child is selected from the group consisting of preterm infants, infants born by Caesarean-section, infants born small for gestational age or with low birth weight, hospitalized infants/young children, infants/young children treated or having been treated by antibiotics, and infants/young children suffering or having suffered from gut infection and/or gut inflammation.

7. The method according to claim 1, wherein the nutritional composition reduces fever and/or use of antipyretics in the infant or young child.

8. A method for reducing fever caused by infection and/or reducing administration of antipyretics in an infant or young child, the method comprising:

administering a nutritional composition comprising at least one fucosylated oligosaccharide and at least one N-acetylated oligosaccharide, wherein the at least one fucosylated oligosaccharide is in a total amount of 0.8-1.5 g/L of the nutritional composition and/or in a total amount of 0.62-1.16 g/100 g of the nutritional composition on a dry weight basis; and the at least one N-acetylated oligosaccharide is in a total amount of 0.5-0.8 g/L of the nutritional composition and/or in a total amount of 0.39-0.62 g/100 g of the nutritional composition on a dry weight basis to the infant or young child in need of same, wherein the infant or young child is being treated by and antibiotic and/or has been treated by an antibiotic, wherein the nutritional composition reduces or decreases an incidence of and/or treats infection 2 weeks to 12 months after termination of the administering of the nutritional composition.

9. The method according to claim 8, wherein the at least one fucosylated oligosaccharide is selected from the group consisting of 2'-fucosyllactose, 3' fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and combinations thereof.

10. The method according to claim 8, wherein the at least one fucosylated oligosaccharide comprises 2'-fucosyllactose, and the at least one N-acetylated oligosaccharide comprises lacto-N-neotetraose (LNnT).

11. The method according to claim 8, wherein the nutritional composition is in a form selected from the group consisting of an infant formula, a starter infant formula, a follow-on or follow-up infant formula, a preterm formula, a baby food, an infant cereal composition, a fortifier and a supplement.

12. The method according to claim 8, wherein the infant or young child is under 6 months of age.

13. The method according to claim 8, wherein the infant or young child is selected from the group consisting of preterm infants, infants born by Caesarean-section, infants born small for gestational age or with low birth weight, hospitalized infants/young children, infants/young children treated or having been treated by antibiotics, and infants/young children suffering or having suffered from gut infection and/or gut inflammation.

14. A method for reducing or decreasing an incidence of and/or treating diseases/conditions involving (i) fever caused by infection and/or (ii) administration of antibiotics and/or (iii) administration of antipyretics in an infant or young child in need thereof, the method comprising:

administering to the infant or young child a nutritional composition comprising at least one fucosylated oligosaccharide and at least one N-acetylated oligosaccharide, wherein the at least one fucosylated oligosaccharide is in a total amount of 0.8-1.5 g/L of the nutritional composition and/or in a total amount of 0.62-1.16 g/100 g of the nutritional composition on a dry weight basis; and the at least one N-acetylated oligosaccharide is in a total amount of 0.5-0.8 g/L of the nutritional composition and/or in a total amount of 0.39-0.62 g/100 g of the nutritional composition on a dry weight basis, wherein the infant or young child is being treated by an antibiotic and/or has been treated by an antibiotic, wherein the nutritional composition reduces or decreases an incidence of and/or treats infection 2 weeks to 12 months after termination of the administering of the nutritional composition.

15. The method according to claim 14, wherein the at least one fucosylated oligosaccharide is selected from the group consisting of 2'-fucosyllactose, 3' fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and combinations thereof.

16. The method according to claim 14, wherein the at least one fucosylated oligosaccharide comprises 2'-fucosyllactose, and the at least one N-acetylated oligosaccharide comprises lacto-N-neotetraose (LNnT).

17. The method according to claim 14, wherein the nutritional composition is in a form selected from the group consisting of an infant formula, a starter infant formula, a follow-on or follow-up infant formula, a preterm formula, a baby food, an infant cereal composition, a fortifier and a supplement.

18. The method according to claim 14, wherein the infant or young child is under 6 months of age.

19. The method according to claim 14, wherein the infant or young child is selected from the group consisting of preterm infants, infants born by Caesarean-section, infants born small for gestational age or with low birth weight, hospitalized infants/young children, infants/young children treated or having been treated by antibiotics, and infants/young children suffering or having suffered from gut infection and/or gut inflammation.

\* \* \* \* \*